United States Patent
Han et al.

(10) Patent No.: US 12,305,188 B2
(45) Date of Patent: May 20, 2025

(54) DUAL HELPER PLASMID

(71) Applicant: NEURACLE GENETICS INC., Seoul (KR)

(72) Inventors: Joo Seok Han, Seoul (KR); Hoon Young Kong, Seoul (KR); Yoon Hyung Hwang, Seoul (KR)

(73) Assignee: NEURACLE GENETICS INC., Seoul (KR)

( * ) Notice: Subject to any disclaimer, the term of this patent is extended or adjusted under 35 U.S.C. 154(b) by 370 days.

(21) Appl. No.: 17/750,241

(22) Filed: May 20, 2022

(65) Prior Publication Data

US 2023/0056355 A1    Feb. 23, 2023

(30) Foreign Application Priority Data

May 27, 2021    (KR) .......................... 10-2021-0068364

(51) Int. Cl.
C12N 15/86    (2006.01)
C07K 14/005    (2006.01)

(52) U.S. Cl.
CPC .... *C12N 15/86* (2013.01); *C12N 2750/14122* (2013.01); *C12N 2750/14143* (2013.01); *C12N 2750/14152* (2013.01)

(58) Field of Classification Search
CPC .......... C12N 15/86; C12N 2750/14122; C12N 2750/14143; C12N 2750/14152; C12N 2710/10322; C07K 14/005
See application file for complete search history.

(56) References Cited

U.S. PATENT DOCUMENTS

| | | | |
|---|---|---|---|
| 12,173,304 | B2 | 12/2024 | Kong et al. |
| 2013/0089523 | A1 | 4/2013 | El-Andaloussi et al. |
| 2021/0147877 | A1 | 5/2021 | Li et al. |

FOREIGN PATENT DOCUMENTS

| | | | |
|---|---|---|---|
| EP | 3722434 | A1 | 10/2020 |
| EP | 4242316 | A1 | 9/2023 |
| GB | 2566572 | A | 3/2019 |
| JP | 2008200043 | A | 9/2008 |
| KR | 1020040033751 | A | 4/2004 |
| WO | WO-2000073480 | A1 | 12/2000 |
| WO | WO-2018192982 | A2 | 10/2018 |
| WO | WO-2019141993 | A1 | 7/2019 |
| WO | WO-2019152816 | A1 | 8/2019 |
| WO | WO-2020086881 | A1 | 4/2020 |

OTHER PUBLICATIONS

Tang et al (2020). Two-Plasmid Packaging System for Recombinant Adeno-Associated Virus. Bio Research Open Access. vol. 9.1, 2020, pp. 219-228. (Year: 2020).*

Collaco et al (1999). A helper virus-free packaging system for recombinant adeno-associated virus vectors. Gene 238 (1999) 397-405. (Year: 1999).*

Grimm et al (2003). Helper Virus-Free, Optically Controllable, and Two-Plasmid-Based Production of Adeno-associated Virus Vectors of Serotypes 1 to 6. Molecular Therapy vol. 7, No. 6, Jun. 2003, pp. 839-850. (Year: 2003).*

Tang et al (2020). Two-Plasmid Packaging System for Recombinant Adeno-Associated Virus. Bio Research Open Access, vol. 9.1, pp. 219-228. (Year: 2020).*

Collaco et al (1999). A helper virus-free packaging system for recombinant adeno-associated virus vectors. Gene, 238 (1999), pp. 397-405. (Year: 1999).*

Grimm et al (2003). Helper Virus-Free, Optically Controllable, and Two-Plasmid-Based Production of Adeno-associated Virus Vectors of Serotypes 1 to 6. Molecular Therapy, vol. 7, No. 6, pp. 839-850. (Year: 2003).*

Grimm, D. and Büning, H., "Small But Increasingly Mighty: Latest Advances in AAV Vector Research, Design, and Evolution," *Hum. Gene Ther.* 28(11): 1075-1086, Mary Ann Liebert, Inc., United States (Nov. 2017).

Grimm, D., et al., "Helper virus-free, optically controllable, and two-plasmid-based production of adeno-associated virus vectors of serotypes 1 to 6," *Mol. Ther.* 7(6): 839-850, Cell Press, United States (Jun. 2003).

Grimm, D., et al., "Novel tools for production and purification of recombinant adeno-associated virus vectors," *Hum. Gene Ther.* 9(18): 2745-2760, Mary Ann Liebert, Inc., United States (Dec. 1998).

Kovesdi, I. and Hedley, S.J., "Adenoviral producer cells," *Viruses* 2(8): 1681-1703, MDPI, Switzerland (Aug. 2010).

Monahan, P.E et al., "Safety of Adeno-Associated Viral gene Therapy Vectors: A Current Evaluation," *Expert Opin. Drug Saf* 1(1):79-91, Ashley Publications, Ltd., United Kingdom (May 2002).

Muzyczka, N., "Use of Adeno-Associated Virus as a General Transduction Vector for Mammalian Cells," *Current Topics in Microbiology and Immunology* 158:98-129, Springer-Verlag Berlin-Heidelberg (Jan. 1992).

Naso, M.F., et al., "Adeno-Associated Virus (AAV) as a Vector for Gene Therapy," *BioDrugs* 31(4):317-334, Springer Nature Switzerland AG (Aug. 2017).

Samulski, R.J. and Muzyczka, N., "AAV-Mediated Gene Therapy for Research and Therapeutic Purposes," *Annu. Rev. Virol.* 1:427-51, Annual Reviews, United States (Nov. 2014).

(Continued)

*Primary Examiner* — Janet L Andres
*Assistant Examiner* — Samadhan Jaising Jadhao
(74) *Attorney, Agent, or Firm* — Sterne, Kessler, Goldstein & Fox P.L.L.C.

(57) ABSTRACT

The present disclosure relates to a dual helper plasmid for producing a recombinant adeno-associated virus. A double transfection method using the dual helper plasmid of the present disclosure is advantageous over the triple transfection method typically used for production of adeno-associated virus in terms of 1) increased chance of co-transfection, 2) increased productivity of recombinant adeno-associated virus, 3) reduction in cost and time of plasmid production and purification, etc., and thus can be usefully utilized for effective production of a gene therapy agent.

23 Claims, 9 Drawing Sheets

Specification includes a Sequence Listing.

(56) References Cited

OTHER PUBLICATIONS

Tang, Q., et al., "Two-Plasmid Packaging System for Recombinant Adeno-Associated Virus," *Biores. Open Access* 9(1): 219-228, Mary Ann Liebert, Inc., United States (Oct. 2020).
Xiao, X., et al., "Production of high-titer recombinant adeno-associated virus vectors in the absence of helper adenovirus," *J. Virology*. 72(3): 2224-2232, American Society for Microbiology, United States (Mar. 1998).
GenBank, "Human adenovirus 5, complete genome," Accession No. AC_000008, accessed at https://www.ncbi.nlm.nih.gov/nuccore/56160529, accessed on Jan. 22, 2025, 13 pages.

\* cited by examiner

DUAL HELPER PLASMID

CROSS-REFERENCE TO RELATED APPLICATION

This application claims the priority benefit of Korean Patent Application No. 10-2021-0068364, filed on May 27, 2021, which is incorporated herein by reference in its entirety.

REFERENCE TO SEQUENCE LISTING SUBMITTED ELECTRONICALLY VIA EFS-WEB

The content of the electronically submitted sequence listing (Name: 4265_0040001_SeqListing_ST25.txt, Size: 34,877 bytes; and Date of Creation: Oct. 25, 2022) submitted in this application is incorporated herein by reference in its entirety.

FIELD OF THE DISCLOSURE

The present disclosure relates to a novel dual helper plasmid for producing a recombinant AAV for gene delivery.

BACKGROUND OF THE DISCLOSURE

Adeno-associated virus (AAV) is a single-stranded DNA virus which belongs to helper-dependent parvoviruses requiring help from adenovirus, etc. for proliferation. It is a non-pathogenic virus having a genome size of about 4.7 kbp and does not induce cell-mediated immune response. The target of infection varies widely depending on serotypes and the virus can deliver genes to non-dividing and dividing cells. In particular, the expression of the genes delivered by the AAV is continued for a long time in vivo. Naso et al., *BioDrug* 31(4): 317-334 (2017); Monahan et al., *Expert Opin Drug Saf,* 1(1): 79-91 (2002); and Conrad et al., *Gene Ther* 3(8): 658-68 (1996).

Typically, recombinant adeno-associated virus is produced by triple transfection of host cells (e.g., HEK293 cells). Xiao et al., *J Virol* 72(3): 2224-32 (1998). It requires 1) an AAV construct plasmid having a gene expression cassette flanked by ITRs (inverted terminal repeats), 2) a "Rep-Cap plasmid" which provides Rep proteins necessary for the replication of the adeno-associated virus genome and capsid proteins that constitute virus particles and, finally, 3) a "helper plasmid" which provides the proteins (E2a, E4) and RNAs (VA RNAs) of adenovirus that help the life cycle of adeno-associated virus. Adeno-associated virus is produced when these three types of plasmids are transfected into HEK293 cells, etc. that provide the E1 and E3 genes of adenovirus. Kovesdi et al., *Viruses* 2(8): 1681-1703 (2010).

The recombinant adeno-associated virus vector is produced only in the cells transfected with all of the above-mentioned three plasmids. If two plasmids are combined as one for double transfection, the chance of co-transfection will increase and, consequently, the production yield of the recombinant adeno-associated virus will be increased. Grimm et al., *Hum Gene Ther* 9(18): 2745-60 (1998); and Grimm et al., *Mol Ther* 7(6): 839-50 (2003). In addition, since the number of the plasmids required to produce the recombinant adeno-associated virus is decreased from three to two, the time and cost required for producing and purifying the plasmids will be saved, too. Tang et al., *Biores Open Access* 9(1): 219-228 (2020).

The recombinant adeno-associated virus vector cannot be replicated in vivo because it does not retain the rep and cap genes and does not have adenovirus-derived genes. Grimm et al., *Hum Gene Ther* 28(11): 1075-1086 (2017).

However, because the relative location of rep, cap, E2, E4 and VA RNA genes in the plasmid varies depending on how the Rep-Cap plasmid and the helper plasmid are combined to prepare a dual helper plasmid, the expression of each gene is affected differently and it is very difficult to expect the effect on productivity.

Accordingly, an engineered dual helper plasmid designed to increase the chance of transfection of a recombinant adeno-associated virus vector and the productivity of a recombinant adeno-associated virus therethrough and, at the same time, reduce the time and cost of the production and purification of a plasmid, and a method for preparing the same are keenly needed.

BRIEF SUMMARY OF THE DISCLOSURE

Provided herein is a dual helper plasmid comprising an E2a gene, E4 gene, VA RNA gene, and rep-cap gene, wherein the E2a, E4, and the VA RNA genes are linked sequentially, and wherein the rep-cap gene is located between the 5'-terminal of the E2a gene and the 3'-terminal of the VA RNA gene in a clockwise direction (from 5' to 3'). In some aspects, the 5'-terminal of the rep-cap gene is linked to the 5'-terminal of the E2a gene, and wherein the 3'-terminal of the rep-cap gene is linked to the 3'-terminal of the VA RNA gene.

Also provided herein is a dual helper plasmid comprising an E2a gene, E4 gene, VA RNA gene, and rep-cap gene, wherein the E2a, E4, and the VA RNA genes are linked sequentially, and wherein the rep-cap gene is located between the 5'-terminal of the E2a gene and the 3'-terminal of the VA RNA gene in a counterclockwise direction (from 3' to 5'). In some aspects, the 3'-terminal of the rep-cap gene is linked to the 5'-terminal of the E2a gene, and wherein the 5'-terminal of the rep-cap gene is linked to the 3'-terminal of the VA RNA gene.

For any of the dual helper plasmids provided herein, such as those described above, in some aspects, the rep-cap gene comprises a rep gene and a cap gene, and wherein the 3'-terminal of the rep gene is linked to the 5'-terminal of the cap gene.

In some aspects, a dual helper plasmid comprises an E2a gene, E4 gene, VA RNA gene, and rep-cap gene, wherein the E2a gene, E4 gene, VA RNA gene, and rep-cap gene are arranged as shown in the cleavage map of FIG. 5A. In some aspects, the E2a gene, E4 gene, VA RNA gene, and rep-cap gene are arranged as shown in the cleavage map of FIG. 5B.

For any of the dual helper plasmids provided herein, such as those described above, in some aspects, the rep gene comprises a rep2 gene derived from adeno-associated virus serotype 2 (AAV2). In some aspects, the rep2 gene comprises the sequence set forth in SEQ ID NO 29.

For any of the dual helper plasmids provided herein, such as those described above, in some aspects, the cap gene comprises a cap gene derived from adeno-associated virus serotype 2 (AAV2; cap2), serotype 5 (AAV5; cap5), serotype 8 (AAV8; cap8), or serotype 9 (AAV9; cap9). In some aspects, the cap gene comprises the sequence set forth in SEQ ID NO 30, SEQ ID NO 31, SEQ ID NO 32, or SEQ ID NO 33.

For any of the dual helper plasmids provided herein, such as those described above, in some aspects, the E2a gene comprises an E2a gene derived from adenovirus serotype 5

(Ad5). In some aspects, the E2a gene comprises the sequence set forth in SEQ ID NO 34.

For any of the dual helper plasmids provided herein, such as those described above, in some aspects, the E4 gene comprises an E4 gene derived from adenovirus serotype 5 (Ad5). In some aspects, the E4 gene comprises the sequence set forth in SEQ ID NO 35.

For any of the dual helper plasmids provided herein, such as those described above, in some aspects, the VA RNA gene comprises a VA RNA gene derived from adenovirus serotype 5 (Ad5). In some aspects, the VA RNA gene comprises the sequence set forth in SEQ ID NO 36.

Provided herein is a dual helper plasmid comprising a regulatory component, wherein the regulatory component comprises (from 5' to 3'): (i) an E2a gene, which comprises the sequence set forth in SEQ ID NO: 34; (ii) an E4 gene, which comprises the sequence set forth in SEQ ID NO: 35; (iii) a VA RNA gene, which comprises the sequence set forth in SEQ ID NO: 36; (iv) a cap gene, which comprises the sequence set forth in SEQ ID NO: 30; and (v) a rep gene, which comprises the sequence set forth in SEQ ID NO: 29.

Provided herein is a dual helper plasmid comprising a regulatory component, wherein the regulatory component comprises (from 5' to 3'): (i) an E2a gene, which comprises the sequence set forth in SEQ ID NO: 34; (ii) an E4 gene, which comprises the sequence set forth in SEQ ID NO: 35; (iii) a VA RNA gene, which comprises the sequence set forth in SEQ ID NO: 36; (iv) a cap gene, which comprises the sequence set forth in SEQ ID NO: 31; and (v) a rep gene, which comprises the sequence set forth in SEQ ID NO: 29.

Provided herein is a dual helper plasmid comprising a regulatory component, wherein the regulatory component comprises (from 5' to 3'): (i) an E2a gene, which comprises the sequence set forth in SEQ ID NO: 34; (ii) an E4 gene, which comprises the sequence set forth in SEQ ID NO: 35; (iii) a VA RNA gene, which comprises the sequence set forth in SEQ ID NO: 36; (iv) a cap gene, which comprises the sequence set forth in SEQ ID NO: 32; and (v) a rep gene, which comprises the sequence set forth in SEQ ID NO: 29.

Provided herein is a dual helper plasmid comprising a regulatory component, wherein the regulatory component comprises (from 5' to 3'): (i) an E2a gene, which comprises the sequence set forth in SEQ ID NO: 34; (ii) an E4 gene, which comprises the sequence set forth in SEQ ID NO: 35; (iii) a VA RNA gene, which comprises the sequence set forth in SEQ ID NO: 36; (iv) a cap gene, which comprises the sequence set forth in SEQ ID NO: 33; and (v) a rep gene, which comprises the sequence set forth in SEQ ID NO: 29.

For the above-described dual helper plasmids, in some aspects, the rep gene and the cap gene are in a clockwise direction. In some aspects, the 5'-terminal of the rep gene is linked to the 5'-terminal of the E2a gene, wherein the 3'-terminal of the rep gene is linked to the 5'-terminal of the cap gene, and wherein the 3'-terminal of the cap gene is linked to 3'-terminal of the VA RNA gene. In some aspects, wherein the rep gene and the cap gene are in a counter-clockwise direction. In some aspects, the 5'-terminal of the rep gene is linked to the 3'-terminal of the VA RNA gene, wherein the 3'-terminal of the rep gene is linked to the 5'-terminal of the cap gene, and wherein the 3'-terminal of the cap gene is linked to the 5'-terminal of the E2a gene.

For any of the dual helper plasmids provided herein (such as those described above), in some aspects, the dual helper plasmid further comprises an antibiotic resistance gene. In some aspects, the antibiotic resistance gene comprises an ampicillin resistance gene, a kanamycin resistance gene, or both. In some aspects, the ampicillin resistance gene comprises the sequence set forth in SEQ ID NO: 37. In some aspects, the kanamycin resistance gene comprises the sequence set forth in SEQ ID NO: 38.

Some aspects of the present disclosure is related to a composition comprising any of the dual helper plasmids described herein.

In some aspects, the composition further comprises an additional plasmid. In some aspects, the additional plasmid is an AAV construct plasmid.

In some aspects, the additional plasmid comprises: (a) an inverted terminal repeat (ITR); (b) a transgene; and (c) a control element operably linked to the transgene. In some aspects, the control element comprises a promoter, enhancer, exon sequence, intron sequence, splicing donor or acceptor sequence, miRNA target sequence, woodchuck hepatitis virus posttranscriptional regulatory element (WPRE) sequence, polyadenylation (pA) sequence, or combinations thereof. In some aspects, the transgene encodes a wild type polypeptide or any variant thereof, a fusion protein, an antibody or an antigen-binding fragment thereof, a RNA-based molecule, or any combination thereof.

Also provided herein is a cell comprising any of the dual helper plasmids of the present disclosure or any of the compositions described herein.

The present disclosure further provides a method of producing a recombinant AAV, comprising modifying a cell to comprise a first plasmid and a second plasmid, wherein the first plasmid is any of the dual helper plasmids described herein, and wherein the second plasmid comprises a transgene. In some aspects, the modifying comprises transfecting the cell with the first plasmid and the second plasmid. In some aspects, wherein the first plasmid and the second plasmid are transfected into the cell concurrently. In some aspects, the first plasmid and the second plasmid are transfected into the cell sequentially. In some aspects, a method of producing a recombinant AAV provided herein further comprises isolating the produced recombinant AAV.

Provided herein is a method of increasing the yield of recombinant AAV during production, comprising modifying a cell to comprise a first plasmid and a second plasmid, wherein the first plasmid is any of the dual helper plasmids described herein, and wherein the second plasmid comprises a transgene, and wherein the amount of recombinant AAV produced after the modifying is increased compared to the corresponding amount produced with a reference method. In some aspects, the reference method comprises modifying a corresponding cell to comprise the following three separate plasmids: i) a Rep-Cap plasmid comprising a gene encoding Rep protein and Cap protein; ii) a helper plasmid comprising a gene encoding the proteins (E2a, E4) and VA RNAs of adenovirus; and iii) an AAV construct plasmid comprising a transgene. In some aspects, the amount of recombinant AAV produced is increased by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, or at least about 50-fold, as compared to the corresponding amount produced using the reference method.

Provided herein is a recombinant AAV produced by any of the methods provided herein. Also provided herein is a pharmaceutical composition comprising any of the recombinant AAV described herein, and a pharmaceutically acceptable excipient.

Some aspects of the present disclosure is related to a method of treating a disease or disorder in a subject in need thereof, comprising administering to the subject any of the recombinant AAV or pharmaceutical formulations provided herein. Also provided herein are recombinant AAV or pharmaceutical formulation for therapy. Also provided herein are recombinant AAV or pharmaceutical formulation for gene therapy. Use of any of the recombinant AAV or pharmaceutical formulation of the present disclosure in the manufacture of a medicament for treating a disease or disorder in a subject in need

BRIEF DESCRIPTION OF THE FIGURES

FIG. 1A schematically shows a pHelper-NG construct for triple transfection, which includes the E2a, E4 gene and VA RNA genes of adenovirus serotype 5. FIGS. 1B-1F schematically show five Helper-In-One-NG plasmid (pHION8) constructs, which are dual helper plasmids prepared by inserting rep2-cap8 gene fragments into different regions of the pHelper-NG construct. FIGS. 1B and 1C schematically show a pHION8-BF construct prepared by cloning a rep2-cap8 construct in a forward direction (clockwise direction, 5'->3') using the BamHI site present between the beginning portion of the E2a gene and the ending portion of the VA RNA gene (FIG. 1B) and a pHION8-BR construct prepared by cloning in a reverse direction (counterclockwise direction, 3'->5') (FIG. 1C). FIGS. 1D and 1E schematically show a pHION8-NF construct prepared by cloning a rep2-cap8 construct in a forward direction using the NotI site present at the beginning portion of the E4 gene (FIG. 1D) and a pHION8-NR construct prepared by cloning in a reverse direction (FIG. 1E). FIG. 1F schematically shows a pHION8-AF construct prepared by cloning a rep2-cap8 construct in a forward direction using the AsiSI site present between the beginning portion of the VA RNA gene and the ending portion of the E4 gene.

FIG. 5A shows a rep-cap gene fragment inserted in a forward direction between the beginning portion of the E2a gene and the ending portion of the VA RNA gene, and FIG. 5B shows the rep-cap gene fragment inserted in a reverse direction.

DETAILED DESCRIPTION OF THE DISCLOSURE

Figure 1A:
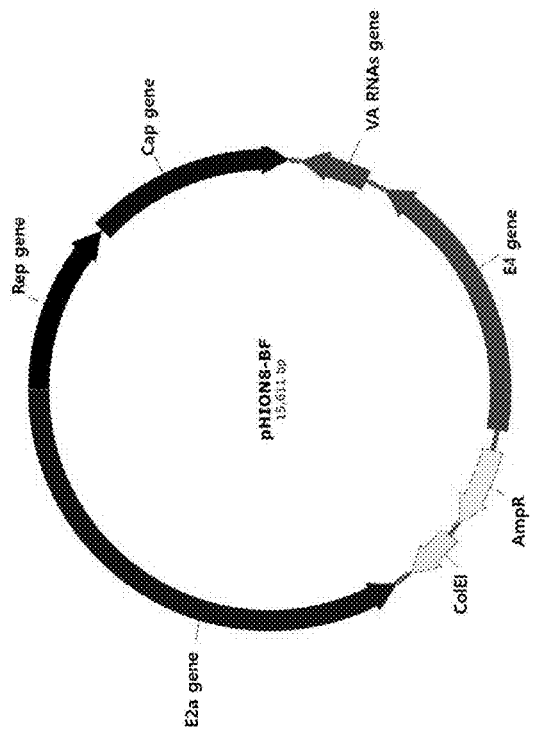
FIGS. 1A-1F show the cleavage maps of pHelper-NG and Helper-In-One constructs (pHION8 series) for producing adeno-associated virus vector serotype 8 (AAV8) prepared by the inventors of the present disclosure.

The present disclosure is generally directed to compositions and methods for producing recombinant AAVs, and the use of such rAAVs to treat a disease or disorder. As described herein, the dual helper plasmids of the present disclosure comprise multiple genes (e.g., E2a gene, E4 gene, VA RNA gene, rep gene, and cap gene). Applicant has identified that by arranging the multiple genes in certain configurations, the yield or productivity can be increased or decreased during recombinant AAV production. Additional aspects of the present disclosure are provided throughout the present application.

I. Definitions

Throughout this disclosure, the term "a" or "an" entity refers to one or more of that entity; for example, "a polypeptide," is understood to represent one or more polypeptides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "at least" prior to a number or series of numbers is understood to include the number adjacent to the term "at least," and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range. "At least" is also not limited to integers (e.g., "at least 5%" includes 5.0%, 5.1%, 5.18% without consideration of the number of significant figures.

It is understood that wherever aspects are described herein with the language "comprising," otherwise analogous aspects described in terms of "consisting of" and/or "consisting essentially of" are also provided. Additionally, for all compositions described herein, and all methods using a composition described herein, the compositions can either comprise the listed components or steps, or can "consist essentially of" the listed components or steps. When a composition is described as "consisting essentially of" the listed components, the composition contains the components listed, and can further contain other components which do not substantially affect the methods disclosed, but do not contain any other components which substantially affect the methods disclosed other than those components expressly listed; or, if the composition does contain extra components other than those listed which substantially affect the methods disclosed, the composition does not contain a sufficient concentration or amount of the extra components to substantially affect the methods disclosed. When a method is described as "consisting essentially of" the listed steps, the method contains the steps listed, and can further contain other steps that do not substantially affect the methods disclosed, but the method does not contain any other steps which substantially affect the methods disclosed other than those steps expressly listed. As a non-limiting specific example, when a composition is described as "consisting essentially of" a component, the composition can additionally contain any amount of pharmaceutically acceptable carriers, vehicles, or diluents and other such components which do not substantially affect the methods disclosed.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAVrh.74, snake AAV, avian AAV, bovine AAV, canine AAV, equine AAV, ovine AAV, goat AAV, shrimp AAV, those AAV serotypes and clades disclosed by Gao et al. (*J. Virol.* 78:6381 (2004)) and Moris et al. (*Virol.* 33:375 (2004)), and any other AAV now known or later discovered. See, e.g., FIELDS et al. VIROLOGY, volume 2, chapter 69 (4th ed., Lippincott-Raven Publishers). In some aspects, an "AAV" includes a derivative of a known AAV. In some aspects, an "AAV" includes a modified or an artificial AAV.

The terms "administration," "administering," and grammatical variants thereof refer to introducing a composition (e.g., a recombinant AAV delivery vector produced using the dual helper plasmids of the present disclosure) into a subject via a pharmaceutically acceptable route. The introduction of a composition into a subject is by any suitable route, including intratumorally, orally, pulmonarily, intranasally, parenterally (intravenously, intra-arterially, intramuscularly, intraperitoneally, or subcutaneously), rectally, intralymphatically, intrathecally, periocularly or topically. Administration includes self-administration and the administration by another. A suitable route of administration allows the composition or the agent to perform its intended function. For example, if a suitable route is intravenous, the composition is administered by introducing the composition or agent into a vein of the subject.

Figure 5A:
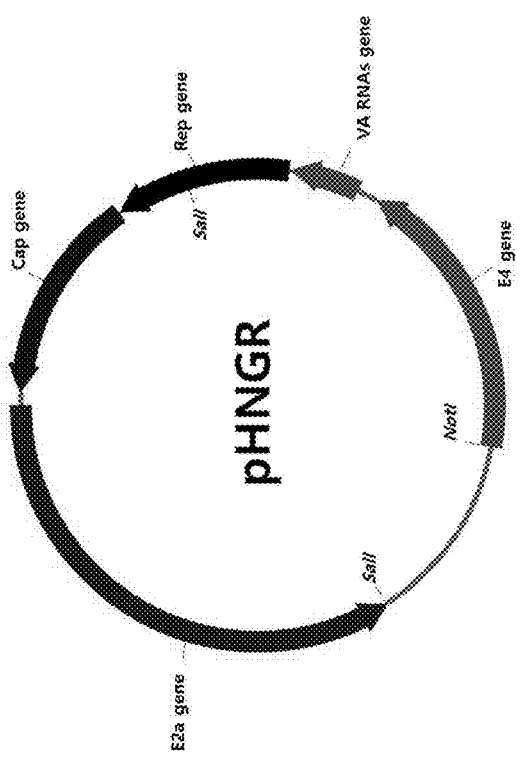
FIGS. 5A and 5B show the cleavage maps of pHNG and pHNGR constructs.
Figure 5B:
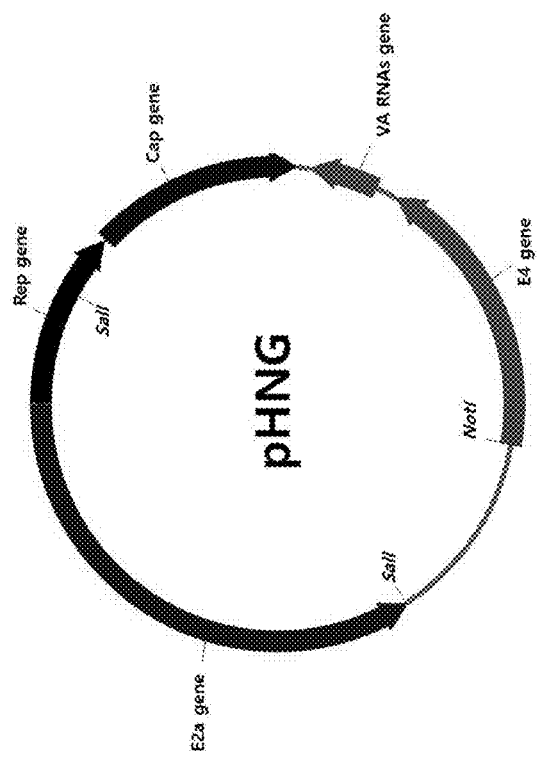

As used herein, the term "antibiotic resistance gene" refers to a gene inserted to a plasmid in order to confer drug resistance so that a microorganism can survive even after exposure to an antibiotic. As described herein, in some aspects, an antibiotic resistance gene can be introduced into a plasmid (e.g., dual helper plasmid) to screen cells having the desired plasmid through cloning. Non-limiting examples of antibiotic resistance genes that are useful for the present disclosure include ampicillin, kanamycin, chloramphenicol, gentamycin, streptomycin, tetracycline, erythromycin, vancomycin, penicillin, spectinomycin, chloramphenicol, sulfadiazine, and trimethoprim resistance genes As further described herein, the dual helper plasmids of the present disclosure comprise rep gene and cap gene which are present with the dual helper plasmids in certain orientation/configuration. In some aspects, the rep and cap genes are in a "clockwise direction," "forward direction," or "5'->3" (e.g., as shown in FIG. 5A), which means that the rep-cap gene is inserted or included in a clockwise direction or in a direction from the site where replication begins (5') to the site where replication ends (3'). In some aspects, the rep and cap genes are in a "counterclockwise direction", "reverse direction" or "3'->5" (e.g., as shown in FIG. 5B) means that the rep-cap gene is inserted or included in a counterclockwise direction or in a direction from the site where replication ends (3') to the site where replication begins (5').

As used herein, the term "rep gene" refers to a gene which encodes one or more open reading frame (ORF), wherein the ORF encodes AAV Rep protein or a mutant or derivative thereof. The AAV Rep protein (or a mutant or derivative thereof) is involved in AAV genome replication and/or AAV genome packaging, and a wild-type rep gene encodes the four Rep proteins Rep78, Rep68, Rep52 and Rep40. Unless indicated otherwise, the term "rep gene" includes a wild-type rep gene, a derivative thereof, and an artificial rep gene having an equivalent function. In some aspects, the rep gene can be a rep2 gene derived from adeno-associated virus serotype 2 (AAV2). In some aspects, the rep2 gene comprises the nucleic acid sequence set forth in SEQ ID NO 29.

As used herein, the term "cap gene" refers to a gene which encodes one or more open reading frame (ORF), wherein the ORF encodes AAV Cap structural protein, or a mutant or derivative thereof. Four proteins are translated from the cap gene. Among them, VP1, VP2 and VP3 proteins are structural proteins constituting AAV particles, and assembly-activating protein (AAP) promotes the formation (assembly) of AAV particles by the structural proteins. Unless indicated otherwise, the term "cap gene" includes a wild-type cap gene, a derivative thereof and an artificial cap gene having an equivalent function. In some aspects, the cap gene is a cap gene derived from adeno-associated virus serotype 2 (AAV2; cap2), serotype 5 (AAV5; cap5), serotype 8 (AAV8; cap8) or serotype 9 (AAV9; cap9). In some aspects, the cap gene comprises the nucleic acid sequence set forth in SEQ ID NO 30 (cap2), SEQ ID NO 31 (cap5), SEQ ID NO 32 (cap8) or SEQ ID NO 33 (cap9).

As used herein, the term "E2a gene" refers to a gene encoding the protein E2a of adenovirus, which regulates the promoter of AAV, helps AAV genome replication and is involved in increased capsid protein production through splicing of Rep mRNA and enhanced stability of capsid mRNA. Unless indicated otherwise, the term "E2a gene" includes a wild-type E2a gene, a derivative thereof and an artificial E2a gene having an equivalent function. In some aspects, the E2a gene is an E2a gene derived from adenovirus serotype 5 (Ad5). In some aspects, the Eta gene comprises the nucleic acid sequence set forth in SEQ ID NO 34.

As used herein, the term "E4 gene" refers to a gene encoding the protein E4 of adenovirus, which is involved in the second-strand synthesis of the AAV genome in the life cycle of AAV and helps AAV genome replication by inhibiting the formation of the MRN (Mre11-Rad50-Nbs1) complex, which is responsible for the intracellular mechanism that inhibits AAV genome replication. Unless indicated otherwise, the term "E4 gene" includes a wild-type E4 gene, a derivative thereof and an artificial E4 gene having an equivalent function. In some aspects, the E4 gene is an E4 gene derived from adenovirus serotype 5 (Ad5). In some aspects, the E4 gene comprises the nucleic acid sequence set forth in SEQ ID NO 35.

As used herein, the term "VA RNA(s) gene" or "VA RNA(s) region" refers to a VA region that produces VA RNA, which increases the stability of AAV capsid mRNA, improves the efficiency of translation and helps preventing the degradation of the Rep52 protein. Unless indicated otherwise, the term "VA RNA gene" includes a wild-type VA RNA gene, a derivative thereof and an artificial VA RNA gene having an equivalent function. In some aspects, the VA RNA gene is a VA RNA gene derived from adenovirus serotype 5 (Ad5). In some aspects, the VA RNA gene comprises the nucleic acid sequence set forth in SEQ ID NO 36.

As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

As used herein, the term "control element" refers to a nucleic acid sequence that regulate (e.g., increase or decrease) the expression of an operably linked nucleic acid (e.g., transgene). Non-limiting examples of suitable control elements are provided elsewhere in the present disclosure.

In some aspects, two or more sequences are said to be "completely conserved" or "identical" if they are 100% identical to one another. In some aspects, two or more sequences are said to be "highly conserved" if they are at least 70% identical, at least 80% identical, at least 90% identical, or at least 95% identical to one another. In some aspects, two or more sequences are said to be "highly conserved" if they are about 70% identical, about 80% identical, about 90% identical, about 95%, about 98%, or about 99% identical to one another. In some aspects, two or more sequences are said to be "conserved" if they are at least 30% identical, at least 40% identical, at least 50% identical, at least 60% identical, at least 70% identical, at least 80% identical, at least 90% identical, or at least 95% identical to one another. In some aspects, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of a polynucleotide or polypeptide or can apply to a portion, region or feature thereof.

As used herein, the term "enhancer" refers to a segment of DNA which contains sequences capable of providing enhanced transcription and in some instances can function independent of their orientation relative to another control sequence. An enhancer can function cooperatively or additively with promoters and/or other enhancer elements.

The terms "excipient" and "carrier" are used interchangeably and refer to an inert substance added to a pharmaceutical composition to further facilitate administration of a compound, e.g., a recombinant AAV delivery vector comprising a transgene and produced using the dual helper plasmids provided herein.

The term "exon" refers to a defined section of nucleic acid that encodes for a protein, or a nucleic acid sequence that is represented in the mature form of an RNA molecule after either portions of a pre-processed (or precursor) RNA have been removed by splicing. The mature RNA molecule can be a messenger RNA (mRNA) or a functional form of a non-coding RNA, such as rRNA or tRNA.

The term "expression," as used herein, refers to a process by which a polynucleotide produces a gene product, e.g., RNA or a polypeptide. It includes, without limitation, transcription of the polynucleotide into messenger RNA (mRNA), and the translation of mRNA into a polypeptide. Expression produces a "gene product" or "encoded protein." As used herein, a gene product can be, e.g., a nucleic acid, such as an RNA produced by transcription of a gene. As used herein, a gene product can be either a nucleic acid or a polypeptide which is translated from a transcript. Gene products described herein further include nucleic acids with post transcriptional modifications, e.g., polyadenylation or splicing, or polypeptides with post translational modifications, e.g., phosphorylation, methylation, glycosylation, the addition of lipids, association with other protein subunits, or proteolytic cleavage.

As used herein, the term "identity" refers to the overall monomer conservation between polymeric molecules, e.g., between polynucleotide molecules. The term "identical" without any additional qualifiers, e.g., polynucleotide A is identical to polynucleotide B, implies the polynucleotide sequences are 100% identical (100% sequence identity). Describing two sequences as, e.g., "70% identical," is equivalent to describing them as having, e.g., "70% sequence identity."

Calculation of the percent identity of two polypeptide or polynucleotide sequences, for example, can be performed by aligning the two sequences for optimal comparison purposes (e.g., gaps can be introduced in one or both of a first and a second polypeptide or polynucleotide sequences for optimal alignment and non-identical sequences can be disregarded for comparison purposes). In some aspects, the length of a sequence aligned for comparison purposes is at least about 30%, at least about 40%, at least about 50%, at least about 60%, at least about 70%, at least about 80%, at least about 90%, at least about 95%, or about 100% of the length of the reference sequence. The amino acids at corresponding amino acid positions, or bases in the case of polynucleotides, are then compared.

When a position in the first sequence is occupied by the same amino acid or nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Suitable software programs that can be used to align different sequences (e.g., polynucleotide sequences) are available from various sources. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at worldwideweb.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In some aspects, the percentage identity (%ID) or of a first amino acid sequence (or nucleic acid sequence) to a second amino acid sequence (or nucleic acid sequence) is calculated as $\%ID=100\times(Y/Z)$, where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

As used herein, the terms "isolated," "purified," "extracted," and grammatical variants thereof are used interchangeably and refer to the state of a preparation of desired composition of the present disclosure, e.g., a polynucleotide comprising a transgene and an untranslated nucleic acid sequence, that has undergone one or more processes of purification. In some aspects, isolating or purifying as used herein is the process of removing, partially removing (e.g., a fraction) a composition of the present disclosure, e.g., a polynucleotide described herein from a sample containing contaminants.

The term "linked," as used herein, refers to a first amino acid sequence or polynucleotide sequence covalently or non-covalently joined to a second amino acid sequence or polynucleotide sequence, respectively. The first amino acid or polynucleotide sequence can be directly joined or juxtaposed to the second amino acid or polynucleotide sequence or alternatively an intervening sequence can covalently join the first sequence to the second sequence. The term "linked" means not only a fusion of a first polynucleotide sequence to a second polynucleotide sequence at the 5'-end or the 3'-end, but also includes insertion of the whole first polynucleotide sequence (or the second polynucleotide sequence) into any two nucleotides in the second polynucleotide sequence (or the first polynucleotide sequence, respectively). The first polynucleotide sequence can be linked to a second polynucleotide sequence by a phosphodiester bond or a linker. The linker can be, e.g., a polynucleotide.

The terms "miRNA," "miR," and "microRNA" are used interchangeably and refer to a microRNA molecule found in eukaryotes that is involved in RNA-based gene regulation. The term will be used to refer to the single-stranded RNA molecule processed from a precursor. In some aspects, the term "antisense oligomers" can also be used to describe the microRNA molecules of the present disclosure. Names of miRNAs and their sequences related to the present disclosure are provided herein. MicroRNAs recognize and bind to target mRNAs through imperfect base pairing leading to destabilization or translational inhibition of the target mRNA and thereby downregulate target gene expression. Conversely, targeting miRNAs via molecules comprising a miRNA binding site (generally a molecule comprising a sequence complementary to the seed region of the miRNA) can reduce or inhibit the miRNA-induced translational inhibition leading to an upregulation of the target gene.

"Nucleic acid," "nucleic acid molecule," "nucleotide sequence," "polynucleotide," and grammatical variants thereof are used interchangeably and refer to a sequence of nucleotides connected by phosphodiester linkages. Polynucleotides are presented herein in the direction from the 5' to the 3' direction. A polynucleotide of the present disclosure can be a deoxyribonucleic acid (DNA) molecule or ribonucleic acid (RNA) molecule. Nucleotide bases are indicated herein by a single letter code: adenine (A), guanine (G), thymine (T), cytosine (C), inosine (I) and uracil (U).

As used herein, the term "operatively linked" or "operably linked" means that DNA sequences to be linked are located adjacent to each other to perform a desired function. For instance, a promoter is operatively linked to a coding region if the promoter helps initiate transcription of the coding sequence (e.g., transgene). As long as this functional relationship is maintained, the promoter needs not be contiguous with the coding region.

The terms "pharmaceutically acceptable carrier," "pharmaceutically acceptable excipient," and grammatical variations thereof, encompass any of the agents approved by a regulatory agency of the U.S. Federal government or listed in the U.S. Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

As used herein, the term "pharmaceutical composition" refers to one or more of the compositions described herein (e.g., polynucleotides, vectors, cells, and/or recombinant viruses) mixed or intermingled with, or suspended in one or more other chemical components, such as pharmaceutically acceptable carriers and excipients.

As used herein, the terms "promoter" and "promoter sequence" are interchangeable and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. In some aspects, a promoter that can be used with the present disclosure includes a tissue specific promoter.

As used herein, the term "gene regulatory region" or "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites, or stem-loop structures. If a coding region is intended for expression in a eukaryotic cell, a polyadenylation signal and transcription termination sequence will usually be located 3' to the coding sequence.

In some aspects, a nucleic acid composition provided herein (e.g., expression construct) can include a promoter and/or other expression (e.g., transcription) control elements operably associated with one or more coding regions. In an operable association a coding region for a gene product is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other expression control elements, besides a promoter, for example enhancers, operators, repressors, and transcription termination signals, can also be operably associated with a coding region to direct gene product expression.

As used herein, the term "transgene" refers to one or more polynucleotide or polynucleotide region encoded into a recombinant expression construct, an expression product of the polynucleotide or polynucleotide region, or a polynucleotide or modulatory (or regulatory) nucleic acid encoding a polypeptide or polypeptides. As further described elsewhere in the present disclosure, in In some aspects, the transgene can be a nucleotide sequence encoding a therapeutic peptide for a particular disease, which is desired to be expressed continuously in the body of a subject or a patient. In some aspects, the term "operatively linked" or "operably linked" means that the DNA sequences to be linked are contiguous so as to perform their desired functions. For example, if a specific promoter helps the initiation of the transcription of a coding sequence (e.g., a transgene), the promoter can be operatively linked to the coding region. The promoter and the coding region do not need to be contiguous as long as this functional relationship is maintained.

In the present disclosure, the term "expression vector" or "expression construct" refers to a vector or a construct including a nucleotide sequence which encodes at least a portion of a transcribed gene product. In some cases, the transcribed RNA molecule is translated into a protein, a polypeptide or a peptide. The expression construct can include various control elements. In addition to a regulatory sequence that regulates transcription and translation, the vector or expression vector can further include a nucleotide sequence that provides another function.

As used herein, the term "subject" refers to an individual to which the AAV (produced using the methods provided herein) or a composition comprising such an AAV is administered. Non-limiting examples include humans, domestic animals (e.g., dogs, cats and the like), farm animals (e.g., cows, sheep, pigs, horses and the like), and laboratory animals (e.g., monkey, rats, mice, rabbits, guinea pigs and the like) for whom diagnosis, treatment, or therapy is desired, particularly humans. The methods described herein are applicable to both human therapy and veterinary applications.

As used herein, the phrase "subject in need thereof" includes subjects, such as mammalian subjects, that would benefit from administration of composition described herein.

As used herein, the term "therapeutically effective amount" is the amount of reagent or pharmaceutical compound comprising a composition of the present disclosure (e.g., polynucleotide comprising a transgene and an untranslated nucleic acid sequence) that is sufficient to a produce a desired therapeutic effect, pharmacologic and/or physiologic effect on a subject in need thereof. A therapeutically effective amount can be a "prophylactically effective amount" as prophylaxis can be considered therapy.

As used herein, the term "transgene" refers to at least one polynucleotide or polynucleotide region encoded in a recombinant expression construct or an expression product of the polynucleotide or polynucleotide region, a polynucleotide encoding a polypeptide or multi-polypeptide or a modulatory or regulatory nucleic acid. In some aspects, the transgene can be heterologous to the cell (i.e., not naturally expressed in the cell) in which it is inserted (or transduced).

The terms "treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also includes prophylaxis or prevention of a disease or condition or its symptoms thereof.

The term "upstream" refers to a nucleotide sequence that is located 5' to a reference nucleotide sequence.

As used herein, the term "vector" or "construct" refers to any vehicle into which a nucleic acid or a gene can be inserted, such as delivery vehicles into which a nucleic acid sequence can be inserted for introduction into a cell where it can be replicated. The nucleic acid sequence which can be inserted into a vector can be exogenous or heterologous. The nucleic acid sequence can be a transgene. Examples of constructs include, but are not limited to, plasmids, cosmids, and viruses (e.g., AAVs). Those skilled in the art can construct the vector or construct through standard recombinant techniques (Maniatis, et al., Molecular Cloning, A Laboratory Manual, Cold Spring Harbor Press, Cold Spring Harbor, N.Y., 1988; and Ausubel et al., In: Current Protocols in Molecular Biology, John, Wiley & Sons, Inc, N.Y., 1994, etc.). As used herein, the term "expression vector" or "expression construct" refers to a vector or construct including a nucleotide sequence coding for at least a portion of a gene product to be transcribed. In some cases, RNA molecules are then translated into a protein, polypeptide or peptide. Expression constructs can include various control elements. In addition to regulatory sequences that govern transcription and translation, vectors and expression vectors can include nucleotide sequence that serve other functions as well.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), β-galactosidase (LacZ), β-glucuronidase (Gus), and the like. Selectable markers can also be considered to be reporters.

II. Dual Helper Plasmids

II.A. E2a Gene, E4 Gene, VA RNA Gene, Rep Gene, and Cap Gene

Some aspects of the present disclosure is directed to dual helper plasmids. As demonstrated herein, such dual helper plasmids can be particularly useful in producing a recombinant adeno-associated virus (AAV) (e.g., comprising a transgene encoding a protein of interest).

Adeno-associated virus (AAV) is a single-stranded DNA virus and a helper-dependent human parvovirus. It has a genome size of about 4.7 kbp. The N-terminal of the genome encodes the rep gene which is involved in viral replication and viral gene expression, and the C-terminal encodes the cap gene which encodes the capsid protein of the virus. Inverted terminal repeats (ITRs) of about 145 bases are inserted at both terminals. The 145-bp ITRs (inverted terminal repeats) having a T-shaped structure function as a replication origin during the replication of the viral genome and serve as a primary packaging signal. The ITRs are the only cis-active base sequences required for making a recombinant AAV construct. Although they have enhancer activity in the presence of the Rep protein, they have minimal activity in the absence of the Rep protein. Thus, an expression construct is prepared with appropriate enhancer, promoter, pA, etc. when cloning a transgene into the recombinant AAV construct (RJ Samulski and N Muzyczka, Annu. Rev. Virolo. 2014. 1:427-451). Four proteins are translated from the rep gene. Their names depict their molecular weights: rep78, rep68, rep52 and rep40. They play an important role in AAV DNA replication. Four proteins are translated from the cap gene. Among them, VP1, VP2 and VP3 proteins are structural proteins constituting AAV particles, and assembly-activating protein (AAP) promotes the formation (assembly) of AAV particles by the structural proteins. For the adeno-associated virus to be replicated effectively, proteins and RNAs derived from a helper virus such as adenovirus or herpes simplex virus are necessary (Muzyczka N. Curr Top Microbiol Immunol 158, 97-129, 1992).

As used herein, "dual helper plasmid" refers to a plasmid that is capable of providing two or more of the requirements for producing AAV in a cell. To produce a recombinant AAV vector comprising a transgene, the following components must be provided to the host cells: (1) transgene, (2) rep and cap proteins, and (3) E2a, E4, and VA RNA proteins. As described elsewhere in the present disclosure, with traditional methods, the different requirements are provided to the cells using three different plasmids (i.e., ① AAV construct plasmid comprising the transgene flanked by ITRs, ② Rep-Cap plasmid, and ③ helper plasmid).

As is apparent from the present disclosure, in some aspects, a dual helper plasmid described herein provides requirements (2) and (3) described above. For instance, in some aspects, the dual helper plasmid comprises a rep gene, cap gene, E2a gene, E4 gene, and VA RNA gene.

As demonstrated herein, dual helper plasmids described herein not only comprise the above-described genes but the genes are also arranged in certain configurations within the plasmid. For instance, in some aspects, the E2a gene, E4 gene, and the VA RNA gene are linked sequentially within the dual helper plasmid, and the rep gene and the cap gene (referred to herein collectively as "rep-cap gene") are between the 5'-terminal of the E2a gene and the 3'-terminal of the VA RNA gene sequentially in a clockwise direction (from 5' to 3'). More specifically, in some aspects, the 5'-terminal of the rep-cap gene is linked to the 5'-terminal of the E2a gene, and wherein the 3'-terminal of the rep-cap gene is linked to the 3'-terminal of the VA RNA gene. A non-limiting example of such a dual helper plasmid is illustrated in FIG. 5A.

In some aspects, the E2a gene, E4 gene, and the VA RNA gene are linked sequentially, and the rep-cap gene is between the 5'-terminal of the E2a gene and the 3'-terminal of the VA RNA gene in a counterclockwise direction (from 3' to 5'). More specifically, in some aspects, the 3'-terminal of the rep-cap gene is linked to the 5'-terminal of the E2a gene, and wherein the 5'-terminal of the rep-cap gene is linked to the 3'-terminal of the VA RNA gene. A non-limiting example of such a dual helper plasmid is illustrated in FIG. 5B.

As is apparent from the present disclosure, in some aspects, each of the E2a gene, E4 gene, and VA RNA gene described above are derived from Adenovirus. In some aspects, the cap gene and the rep gene are derived from the same AAV serotype. For instance, in some aspects, both the cap gene and the rep gene are derived from AAV2 (see, e.g., pUC-R2C2 construct described in Example 1-4). In some aspects, the cap gene and the rep gene are derived from AAVs having different serotype. For instance, as demonstrated herein, in some aspects, the cap gene is derived from AAV8 (cap8 or a fragment thereof) and the rep gene is derived from AAV2 (rep2 or a fragment thereof) (see, e.g., pUC-R2C8 construct described in Example 1-2). In some aspects, the cap gene is derived from AAV9 (cap9 or a fragment thereof) and the rep gene is derived from AAV2 (rep2 or a fragment thereof) (see, e.g., pUC-R2C9 construct described in Example 1-6). In some aspects, the cap gene is derived from AAV5 (cap8 or a fragment thereof) and the rep gene is derived from AAV2 (rep2 or a fragment thereof) (see, e.g., pUC-R2C5 construct described in Example 1-7).

Non-limiting examples of types or serotypes of the AAV that can be used in the present disclosure include AAVrh.10 (AAVrh10), AAV-DJ (AAVDJ), AAV-DJ8 (AAVDJ8), AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh. 52, AAV3-11/rh.53, AAV4-8/ rh11.64, AAV4-9/rh.54, AAV4-19/rh. 55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu. 15, AAV33.8/hu. 16, AAV52/hu. 19, AAV52.1/hu.20, AAV58.2/hu.25, AAVA3.3, AAV A3.4, AAVA3.5, AAV A3.7, AAVC1, AAVC2, AAVCS, AAVF3, AAVFS, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhEr1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC 8, AAV-PAEC 11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, B P61 AAV, B P62 AAV, B P63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV10, Japanese AAV10 serotype, and any combinations thereof.

In some aspects, the serotype of the adeno-associated virus useful for the present disclosure comprises AAV1, AAV2, AAV3, AAV4, AAV5, AAV6, AAV7, AAV8, AAV9, AAVrh10, or a combination thereof. Accordingly, in some aspects, one or more of the multiple genes of a dual helper plasmid are derived from AAV1. For instance, in some aspects, the rep gene is derived from AAV1. In some aspects, the cap gene is derived from AAV1. In some aspects, both the rep gene and the cap gene are derived from AAV1. In some aspects, one or more of the multiple genes of a dual helper plasmid are derived from AAV2. For instance, in some aspects, the rep gene is derived from AAV2. In some aspects, the cap gene is derived from AAV2. In some aspects, both the rep gene and the cap gene are derived from AAV2. In some aspects, one or more of the multiple genes of a dual helper plasmid are derived from AAV3. For instance, in some aspects, the rep gene is derived from AAV3. In some aspects, the cap gene is derived from AAV3. In some aspects, both the rep gene and the cap gene are derived from AAV3. In some aspects, one or more of the multiple genes of a dual helper plasmid are derived from AAV4. For instance, in some aspects, the rep gene is derived from AAV4. In some aspects, the cap gene is derived from AAV4. In some aspects, both the rep gene and the cap gene are derived from AAV4. In some aspects, one or more of the multiple genes of a dual helper plasmid are derived from AAV5. For instance, in some aspects, the rep gene is derived from AAV5. In some aspects, the cap gene is derived from AAV5. In some aspects, both the rep gene and the cap gene are derived from AAV5. In some aspects, one or more of the multiple genes of a dual helper plasmid are derived from AAV6. For instance, in some aspects, the rep gene is derived from AAV6. In some aspects, the cap gene is derived from AAV6. In some aspects, both the rep gene and the cap gene are derived from AAV6. In some aspects, one or more of the multiple genes of a dual helper plasmid are derived from AAV7. For instance, in some aspects, the rep gene is derived from AAV7. In some aspects, the cap gene is derived from AAV7. In some aspects, both the rep gene and the cap gene are derived from AAV7. In some aspects, one or more of the multiple genes of a dual helper plasmid are derived from AAV8. For instance, in some aspects, the rep gene is derived from AAV8. In some aspects, the cap gene is derived from AAV8. In some aspects, both the rep gene and the cap gene are derived from AAV8. In some aspects, one or more of the multiple genes of a dual helper plasmid are derived from AAV9. For instance, in some aspects, the rep gene is derived from AAV9. In some aspects, the cap gene is derived from AAV9. In some aspects, both the rep gene and the cap gene are derived from AAV9. In some aspects, one or more of the multiple genes of a dual helper plasmid are derived from AAVrh10. For instance, in some aspects, the rep gene is derived from AAVrh10. In some aspects, the cap gene is derived from AAVrh10. In some aspects, both the rep gene and the cap gene are derived from AAVrh10.

To further illustrate, in some aspects, a dual helper plasmid of the present disclosure comprises E2a gene, E4 gene, VA RNA gene, rep gene, and cap gene, wherein the rep gene is derived from AAV2. The nucleic acid sequence for the AAV2 rep gene is set forth in SEQ ID NO: 29. In some aspects, a dual helper plasmid comprises E2a gene, E4 gene, VA RNA gene, rep gene, and cap gene, wherein the rep gene comprises a nucleic acid sequence that has at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to the sequence set forth in SEQ ID NO: 29. In some aspects, a dual helper plasmid comprises E2a gene, E4 gene, VA RNA gene, rep gene, and cap gene, wherein the rep gene comprises the nucleic acid sequence set forth in SEQ ID NO: 29.

In some aspects, a dual helper plasmid described herein comprises E2a gene, E4 gene, VA RNA gene, rep gene, and cap gene, wherein the cap gene is derived from AAV2, AAV5, AAV8, or AAV9.

In some aspects, the cap gene is derived from AAV2. Accordingly, in some aspects, a dual helper plasmid described herein comprises a rep gene derived from AAV2 (rep2) and a cap gene derived from AAV2 (cap2). The nucleic acid sequence for the AAV2 cap gene is set forth in SEQ ID NO: 30. In some aspects, a dual helper plasmid comprises E2a gene, E4 gene, VA RNA gene, rep gene, and cap gene, wherein the cap gene comprises a nucleic acid sequence that has at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity the sequence set forth in SEQ ID NO: 30. In some aspects, a dual helper plasmid comprises E2a gene, E4 gene, VA RNA gene, rep gene, and cap gene, wherein the cap gene comprises the nucleic acid sequence set forth in SEQ ID NO: 30.

In some aspects, the cap gene is derived from AAV5. For instance, in some aspects, a dual helper plasmid described herein comprises a rep gene derived from AAV2 (rep2) and a cap gene derived from AAV5 (cap5). The nucleic acid sequence for the AAV5 cap gene is set forth in SEQ ID NO: 31. In some aspects, a dual helper plasmid comprises E2a gene, E4 gene, VA RNA gene, rep gene, and cap gene, wherein the cap gene comprises a nucleic acid sequence that has at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity the sequence set forth in SEQ ID NO: 31. In some aspects, a dual helper plasmid comprises E2a gene, E4 gene, VA RNA gene, rep gene, and cap gene, wherein the cap gene comprises the nucleic acid sequence set forth in SEQ ID NO: 31.

In some aspects, the cap gene is derived from AAV8. For instance, in some aspects a dual helper plasmid described herein comprises a rep gene derived from AAV2 (rep2) and a cap gene derived from AAV8 (cap8). The nucleic acid sequence for the AAV8 cap gene is set forth in SEQ ID NO: 32. In some aspects, a dual helper plasmid comprises E2a gene, E4 gene, VA RNA gene, rep gene, and cap gene, wherein the cap gene comprises a nucleic acid sequence that has at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity the sequence set forth in SEQ ID NO: 32. In some aspects, a dual helper plasmid comprises E2a gene, E4 gene, VA RNA gene, rep gene, and cap gene, wherein the cap gene comprises the nucleic acid sequence set forth in SEQ ID NO: 32.

In some aspects, the cap gene is derived from AAV9. For instance, in some aspects a dual helper plasmid described herein comprises a rep gene derived from AAV2 (rep2) and a cap gene derived from AAV9 (cap9). The nucleic acid sequence for the AAV9 cap gene is set forth in SEQ ID NO: 33. In some aspects, a dual helper plasmid comprises E2a gene, E4 gene, VA RNA gene, rep gene, and cap gene, wherein the cap gene comprises a nucleic acid sequence that has at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity the sequence set forth in SEQ ID NO: 33. In some aspects, a dual helper plasmid comprises E2a gene, E4 gene, VA RNA gene, rep gene, and cap gene, wherein the cap gene comprises the nucleic acid sequence set forth in SEQ ID NO: 33.

In some aspects, a dual helper plasmid provided herein comprises E2a gene, E4 gene, VA RNA gene, rep gene, and cap gene, wherein the E2a gene is derived from adenovirus serotype 5 (Ad5). The nucleic acid sequence for the Ad5 E2a gene is set forth in SEQ ID NO: 34. Accordingly, in some aspects, a dual helper plasmid useful for the present disclosure comprises E2a gene, E4 gene, VA RNA gene, rep gene, and cap gene, wherein the E2a gene comprises a nucleic acid sequence that has at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity the sequence set forth in SEQ ID NO: 34. In some aspects, a dual helper plasmid comprises E2a gene, E4 gene, VA RNA gene, rep gene, and cap gene, wherein the E2a gene comprises the nucleic acid sequence set forth in SEQ ID NO: 34.

In some aspects, a dual helper plasmid provided herein comprises E2a gene, E4 gene, VA RNA gene, rep gene, and cap gene, wherein the E4 gene is derived from adenovirus serotype 5 (Ad5). The nucleic acid sequence for the Ad5 E4 gene is set forth in SEQ ID NO: 35. Accordingly, in some aspects, a dual helper plasmid useful for the present disclosure comprises E2a gene, E4 gene, VA RNA gene, rep gene, and cap gene, wherein the E4 gene comprises a nucleic acid sequence that has at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity the sequence set forth in SEQ ID NO: 35. In some aspects, a dual helper plasmid comprises E2a gene, E4 gene, VA RNA gene, rep gene, and cap gene, wherein the E4 gene comprises the nucleic acid sequence set forth in SEQ ID NO: 35.

In some aspects, a dual helper plasmid provided herein comprises E2a gene, E4 gene, VA RNA gene, rep gene, and cap gene, wherein the VA RNA gene is derived from adenovirus serotype 5 (Ad5). The nucleic acid sequence for the Ad5 VA RNA gene is set forth in SEQ ID NO: 36. Accordingly, in some aspects, a dual helper plasmid useful for the present disclosure comprises E2a gene, E4 gene, VA RNA gene, rep gene, and cap gene, wherein the VA RNA gene comprises a nucleic acid sequence that has at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity the sequence set forth in SEQ ID NO: 36. In some aspects, a dual helper plasmid comprises E2a gene, E4 gene, VA RNA gene, rep gene, and cap gene, wherein the VA RNA gene comprises the nucleic acid sequence set forth in SEQ ID NO: 36.

As is apparent from the present disclosure, in some aspects, the dual helper plasmids described herein comprise genes derived from the same viral source or from multiple viral sources. In some aspects, a dual helper plasmid described comprises: (i) an E2a gene derived from Ad5 (e.g., SEQ ID NO: 34); (ii) an E4 gene derived from Ad5 (e.g., SEQ ID NO: 35); (iii) a VA RNA gene derived from Ad5 (e.g., SEQ ID NO: 36), (iv) a cap gene derived from AAV2 (e.g., SEQ ID NO: 30); and (v) a rep gene derived from AAV2 (e.g., SEQ ID NO: 29). In some aspects, a dual helper plasmid described comprises: (i) an E2a gene derived from Ad5 (e.g., SEQ ID NO: 34); (ii) an E4 gene derived from Ad5 (e.g., SEQ ID NO: 35); (iii) a VA RNA gene derived from Ad5 (e.g., SEQ ID NO: 36), (iv) a cap gene derived from AAV5 (e.g., SEQ ID NO: 31); and (v) a rep gene derived from AAV2 (SEQ ID NO: 29). In some aspects, a dual helper plasmid described comprises: (i) an E2a gene derived from Ad5 (e.g., SEQ ID NO: 34); (ii) an E4 gene derived from Ad5 (e.g., SEQ ID NO: 35); (iii) a VA RNA gene derived from Ad5 (e.g., SEQ ID NO: 36), (iv) a cap gene derived from AAV8 (e.g., SEQ ID NO: 32); and (v) a rep gene derived from AAV2 (e.g., SEQ ID NO: 29). In some aspects, a dual helper plasmid described comprises: (i) an E2a gene derived from Ad5 (e.g., SEQ ID NO: 34); (ii) an E4 gene derived from Ad5 (e.g., SEQ ID NO: 35); (iii) a VA RNA gene derived from Ad5 (e.g., SEQ ID NO: 36), (iv) a cap gene derived from AAV9 (e.g., SEQ ID NO: 33); and (v) a rep gene derived from AAV2 (e.g., SEQ ID NO: 29).

As described and demonstrated herein, the arrangement of one or more of the genes described above (e.g., E2a gene, E4 gene, VA RNA gene, rep gene, and cap gene) can help improve certain properties of the dual helper plasmids of the present disclosure. For instance, in some aspects, a dual helper plasmid described comprises: (i) an E2a gene derived from Ad5 (e.g., SEQ ID NO: 34); (ii) an E4 gene derived from Ad5 (e.g., SEQ ID NO: 35); (iii) a VA RNA gene derived from Ad5 (e.g., SEQ ID NO: 36), (iv) a cap gene derived from AAV2, AAV5, AAV8, or AAV9 (e.g., SEQ ID NO: 30, SEQ ID NO: 31, SEQ ID NO: 32, or SEQ ID NO: 33, respectively); and (v) a rep gene derived from AAV2 (e.g., SEQ ID NO: 29), wherein the rep gene and the cap gene are in a clockwise direction. For instance, in some aspects, the 5'-terminal of the rep gene is linked to the 5'-terminal of the E2a gene, wherein the 3'-terminal of the rep gene is linked to the 5'-terminal of the cap gene, and wherein the 3'-terminal of the cap gene is linked to 3'-terminal of the VA RNA gene. See, e.g., FIG. 5A. In some aspects, a dual helper plasmid described comprises: (i) an E2a gene derived from Ad5 (e.g., SEQ ID NO: 34); (ii) an E4 gene derived from Ad5 (e.g., SEQ ID NO: 35); (iii) a VA RNA gene derived from Ad5 (e.g., SEQ ID NO: 36), (iv) a cap gene derived from AAV2, AAV5, AAV8, or AAV9 (e.g., SEQ ID NO: 30, SEQ ID NO: 31, SEQ ID NO: 32, or SEQ ID NO: 33, respectively); and (v) a rep gene derived from AAV2 (e.g., SEQ ID NO: 29), wherein the rep gene and the cap gene are in a counterclockwise direction. In some aspects, the 5'-terminal of the rep gene is linked to the 3'-terminal of the VA RNA gene, wherein the 3'-terminal of the rep gene is linked to the 5'-terminal of the cap gene, and wherein the 3'-terminal of the cap gene is linked to the 5'-terminal of the E2a gene. See, e.g., FIG. 5B.

Based on at least the features described herein (e.g., the particular arrangements of the E2a gene, E4 gene, VA RNA gene, rep gene, and cap gene), the dual helper plasmid of the present disclosure exhibit one or more of the following improved properties: 1) increased chance of co-transfection such that host cell has all the necessary components to produce a recombinant AAV, 2) increased productivity of recombinant adeno-associated virus, and 3) reduction in cost and time of plasmid production and purification. Additional disclosure relating to such properties are provided elsewhere in the present disclosure.

II.B. Additional Features

As is apparent from the present disclosure, in some aspects, the dual helper plasmids described herein comprise one or more additional features that are useful in a recombinant AAV production. For instance, in some aspects, the dual helper plasmid described herein further includes an antibiotic resistance gene. For instance, in some aspects, the dual helper plasmids further comprises a selection marker. As used herein, the term "selection marker" refers to any gene that can be used to identify cells that express a nucleic acid sequence. Accordingly, such selection marker can be used to identify and enrich for the transformed cells after transfection with the dual helper plasmids described herein. The selection markers that can be used with the present disclosure include any suitable selection markers known in the art. Non-limiting examples of suitable selection markers include (i) enzymes encoding resistance to an antibiotic (i.e., "antibiotic resistance gene"), e.g., kanamycin, neomycin, puromycin, hygromycin, blasticidin, or zeocin; or (ii) fluorescent proteins, for example green fluorescent protein (GFP), red fluorescent protein (RFP) or blue fluorescent protein (BFP).

In some aspects, the selection marker comprises an antibiotic resistance gene. In some aspects, the antibiotic resistance gene comprises an ampicillin resistance gene, kanamycin resistance gene, or both. The nucleic acid sequence for the ampicillin resistance gene is set forth in SEQ ID NO 37. The nucleic acid sequence for the kanamycin resistance gene is set forth in SEQ ID NO 38.

III. Expression Construct

As is apparent from the present disclosure, in some aspects, the dual helper plasmids provided herein can be used in combination with one or more additional plasmids, e.g., in producing a recombinant AAV. In some aspects, the additional plasmid comprises a recombinant expression construct, e.g., an AAV construct plasmid (referred to herein as "expression construct"). Exemplary aspects of such expression constructs are described below.

III.A. Transgene (e.g., Flanked by ITRs)

As further described elsewhere in the present disclosure, in some aspects, a dual helper plasmid provided herein comprises a E2a gene, E4 gene, VA RNA gene, rep gene, and cap gene. In such aspects, the transgene (e.g., which is to be introduced into the recombinant AAV that is produced) can be provided by a separate expression construct (e.g., AAV construct plasmid). Accordingly, in some aspects, the expression construct comprises a transgene. In some aspects, the transgene is flanked by inverted terminal repeats (ITRs). Transgenes useful for the present disclosure is not particularly limited as long as the transgene can be translated into a polypeptide when introduced into a cell. Accordingly, any suitable transgenes of interest can be used with present disclosure. In some aspects, a transgene encodes a polypeptide (or any variant thereof), fusion protein, antibody or an antigen-binding fragment thereof, a RNA-based molecule (e.g., miRNA, shRNA, ribozyme, siRNA), or any combination thereof.

In some aspects, a transgene encodes a protein that is useful for the treatment of a disease or disorder, such as those described herein. In some aspects, the transgene encodes a therapeutic peptide for a specific disease for the purpose of sustained expression in the body of a subject or patient.

III.B. Control Elements

In some aspects, the expression construct that can be used with the dual helper plasmids of the present disclosure further comprises a control element. In some aspects, the control element is operably linked to the transgene.

Accordingly, in some aspects, an expression construct described herein (e.g., AAV construct plasmid) comprises:
(a) an ITR (inverted terminal repeat);
(b) a transgene; and
(c) a control element operably linked to the transgene.

Control elements useful for the present disclosure comprises an enhancer (e.g., CMV enhancer), a promoter (e.g., CMV promoter, EF-1α promoter, β-actin promoter), an exon (e.g., exon 1, exon 2), an intron (e.g., intron A), a splicing donor or acceptor sequence, or combinations thereof. In some aspects, the control element can include a sequence for transcription termination (e.g., poly A), a sequence for stable transgene expression (e.g., WPRE sequence), a sequence for reducing transgene-specific immunity (e.g., miRNA target sequence), or combinations thereof. Details about the transgene and the control element (ITR sequence, enhancer sequence, promoter sequence, E1 sequence, splicing donor sequence, EF-1α intron or its fragment sequence including splicing acceptor, EF-1α E2 sequence, WPRE sequence, miR sequence, poly A sequence, etc.) can be found in US 2022/0010332 A1, which is incorporated herein by reference in its entirety.

As described above, in some aspects, an expression construct useful for the present disclosure comprises (i) a transgene and (ii) a control element operably linked to the transgene, wherein the control element includes the following components:
1) a CMV enhancer sequence;
2) a CMV promoter sequence, EF-1α promoter sequence, or chicken β-actin promoter sequence;
3) a CMV E1 sequence, EF-1α E1 sequence, or chicken β-actin E1 sequence;
4) a splicing donor sequence;
5) an EF-1α intron fragment sequence; and
6) an EF-1α E2 sequence.

IV. Vectors

In some aspects, provided herein are vectors, e.g., comprising any of the plasmids provided herein (e.g., dual helper plasmid and/or expression construct comprising a transgene). Also provided herein are recombinant AAVs produced using the plasmids provided herein. As described herein, such vectors are useful for recombinant expression in host cells and cells targeted for therapeutic intervention.

As is apparent from the present disclosure, in some aspects, vectors useful for the present disclosure are derived from AAV. AAV possesses unique features that make it attractive as a vector system for delivering foreign DNA into cells. AAV infection of cells in culture has generally been non-cytopathic, and natural infection of humans and other animals is silent and asymptomatic. Moreover, AAV infects many different types of mammalian cells allowing the possibility of targeting many different tissues in vivo. AAV also possesses additional advantages that make it a particularly attractive viral system for gene delivery, including the promotion of an immune response that is relatively mild compared to other forms of gene delivery, and persistent expression in both dividing and quiescent cells based on non-integrating, episomal vector DNA. Also, AAV withstands the conditions used to inactivate adenovirus (56° to 65° C. for several hours), making cold preservation of rAAV-based vaccines less critical.

Non-limiting examples of the types or serotypes of adeno-associated viruses that can be used with the present disclosure are provided elsewhere in the present disclosure.

V. Cells

In some aspects, the present disclosure provides cells comprising the plasmids described herein (e.g., dual helper plasmid and expression construct comprising a transgene) (also referred to herein as "modified cells"). In some aspects, the cells (e.g., a host cell) have been transfected with a dual helper plasmid and an AAV construct plasmid to produce a recombinant AAV. As described herein, in some aspects, the modified cells of the present disclosure (e.g., comprising a dual helper plasmid and an expression construct comprising a transgene) are capable of improving one or more aspects of recombinant AAV production. For instance, in some aspects, the modified cells provided herein allow for greater yield when producing a recombinant AAV, as compared to a reference cell. In some aspects, the reference cell comprises a corresponding cell that was modified to comprise the following three separate plasmids: (1) first plasmid comprising a rep gene and a cap gene ("rep-cap plasmid"); (2) second plasmid comprising an Eta gene, E4 gene, and VA RNA gene ("helper plasmid"); and (3) third plasmid comprising a transgene.

In some aspects, compared to the reference cell, cells of the present disclosure (e.g., comprising a dual helper plasmid and an expression vector comprising a transgene) are capable of increasing the amount of recombinant AAV produced by at least about 10%, at least about 20%, at least about 30%, at least about 40%, at least about 50%, at least about 60%, at least about 70%, at least about 80%, at least about 90%, at least about 100% or more. In some aspects, compared to the reference cells, cells of the present disclosure are capable of increasing the amount of recombinant AAV produced by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 75-fold, or at least about 100-fold or more. In some aspects, cells provided herein (e.g., modified to comprise a dual helper plasmid and an expression construct comprising a transgene) allow for reduced production and/or purification time compared to the reference cells. In some aspects, compared to the reference cell, the production and/or purification time is decreased by at least about 10%, at least about 20%, at least about 30%, at least about 40%, at least about 50%, at least about 60%, at least about 70%, at least about 80%, at least about 90%, or at least about 95% or more.

As is apparent from the present disclosure, also provided herein are cells provided herein have been modified (e.g., transfected) to comprise the recombinant AAV produced using the plasmids described herein. Such cells can be particularly useful for producing a protein, e.g., encoded by a transgene described herein. Not to be bound by any one theory, in some aspects, when a cell (e.g., host cell) is transfected with the plasmids described herein (e.g., dual helper plasmid and expression construct comprising a transgene operably linked to a control element), the resulting recombinant AAV produced comprises one of more features of the individual plasmids. For instance, in some aspects, the resulting recombinant AAV comprises the transgene operably linked to the control element.

As described herein, in some aspects, the one or more control elements described herein can enhance the expression of the protein encoded by the transgene ("encoded protein") in a cell. Accordingly, in some aspects, a cell described herein (e.g., transfected with a recombinant AAV delivery vector comprising a transgene operably linked to one or more control elements described herein) produces greater expression of the encoded protein compared to a reference cell. In some aspects, the reference cell is transfected with a corresponding delivery vector but lacking one or more of the control elements described herein.

In some aspects, the cells described herein are modified (e.g., transfected) in vitro to produce a composition of interest. For instance, in some aspects, the cells are transfected in vitro with a dual helper plasmid and an expression construct (e.g., such as those described herein) to produce a recombinant AAV. In some aspects, the cells are transfected in vitro with the recombinant gene delivery vector to produce the protein encoded by the transgene. In some aspects, the cells described herein can produce the encoded protein in vivo (e.g., in a subject that received an administration of the recombinant AAV comprising the transgene). In some aspects, the cells described herein can produce the composition of interest (e.g., encoded protein) both in vitro and in vivo.

As described herein, in some aspects, the present disclosure provides a host cell transformed, transduced or transfected with, e.g., the recombinant expression construct for transgene expression. As used herein, the term "host cell" includes eukaryotic cells and prokaryotic cells, and refers to a cell of an organism that can be transduced, e.g., so that a gene encoded by a plasmid or an expression construct (e.g., AAV construct plasmid, Rep-Cap plasmid, helper plasmid, dual helper plasmid, etc.) can be expressed or replicated. In some aspects, it refers to an isolated (eukaryotic) host cell. As used herein, the term "transfection" is intended to include transduction and transformation. The host cell can be transfected, transduced, or transformed with any of the plasmids, constructs, and/or vectors described herein. The term means a process whereby an exogenous nucleic acid molecule is delivered or introduced into the host cell.

In some aspects, the host cell is a eukaryotic cell. In some aspects, the host cell is selected from the group consisting of a mammalian cell, an insect cell, a yeast cell, a transgenic mammalian cell, and a plant cell. In some aspects, the host cell is a prokaryotic cell. In some aspects, the prokaryotic cell is a bacterial cell.

In some aspects, cells useful for the present disclosure (e.g., host cells) comprise an insect cell, a mammalian cell, or both. In some aspects, the insect cell can be Sf9 cell. In some aspects, the mammalian cell comprises HEK293 cell, HeLa cell, ARPE-19 cell, RPE-1 cell, HepG2 cell, Hep3B cell, Huh-7 cell, C8D1a cell, Neuro2A cell, CHO cell, MES13 cell, BHK-21 cell, COST cell, COPS cell, A549 cell, MCF-7 cell, HC70 cell, HCC1428 cell, BT-549 cell, PC3 cell, LNCaP cell, Capan-1 cell, Panc-1 cell, MIA PaCa-2 cell, SW480 cell, HCT166 cell, LoVo cell, A172 cell, MKN-45 cell, MKN-74 cell, Kato-III cell, NCI-N87 cell, HT-144 cell, SK-MEL-2 cell, SH-SY5Y cell, C6 cell, HT-22 cell, PC-12 cell, NIH3T3 cell, or combinations thereof.

In some aspects, a cell useful for the present disclosure comprises a human cell. In some aspects, the human cell is a cell of a subject that is to receive an administration of a recombinant gene delivery vector described herein. In some aspects, the human cell is from a donor (e.g., healthy human subject).

VI. Composition

The present disclosure is also directed to compositions comprising the dual helper plasmids described herein. As is apparent from the present disclosure, in some aspects, such compositions further comprise an additional plasmid, such as the expression constructs described herein (e.g., an AAV construct plasmid for transgene expression). As further described elsewhere in the present disclosure, such compositions can be useful in producing a recombinant AAV.

The various plasmids (e.g., dual helper plasmid), constructs (e.g., expression construct), vectors (e.g., recombinant AAV delivery vector), and cells disclosed herein (also referred to herein as "active compounds") can be incorporated into pharmaceutical compositions suitable for administration. Accordingly, in some aspects, the present disclosure is directed to such pharmaceutical compositions. For instance, in some aspects, the present disclosure provides a pharmaceutical composition comprising a recombinant AAV produced using the plasmids described herein (e.g., dual helper plasmids).

In some aspects, the pharmaceutical compositions described herein further comprises a pharmaceutically acceptable carrier.

The pharmaceutically acceptable carriers that can be used with the present disclosure include those that are commonly used for formulation. Non-limiting examples of such pharmaceutically acceptable carriers include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and combinations thereof. The pharmaceutical compositions of the present disclosure can further comprise one or more additives, such as a lubricant, a wetting agent, sweetener, a flavorant, an emulsifier, a suspending agent, a preservative, and combinations thereof. Additional details of suitable pharmaceutically acceptable carriers and formulations are described in Remington's Pharmaceutical Sciences (19th ed., 1995).

A pharmaceutical composition of the disclosure is formulated to be compatible with an intended route of administration. Non-limiting examples of such administration routes are provided elsewhere in the present disclosure.

The pharmaceutical compositions described herein can be provided as a single-dosage or in multiple-dosage forms. In some aspects, a pharmaceutical composition provided herein is formulated in the form of a solution (e.g., in an oily or aqueous medium), a suspension, an emulsion, an extract, a powder, a granule, a tablet or a capsule. In some aspects, a formulation comprising a pharmaceutical composition described herein can further contain a dispersant, a stabilizer, or both.

VII. Kits

Also disclosed herein are kits comprising one or more of the various plasmids (e.g., dual helper plasmid), constructs (e.g., expression construct), vectors (e.g., recombinant AAV delivery vector), cells, and compositions (e.g., pharmaceutical compositions) disclosed herein. In some aspects, the kit also comprises instructions for use (e.g., for administering any of the aforesaid, or a combination thereof, to a subject in need thereof).

The terms "kit" and "system," as used herein, are intended to refer to at least one or more of the various plasmids (e.g., dual helper plasmid), constructs (e.g., expression construct), vectors (e.g., recombinant AAV delivery vector), cells, and compositions (e.g., pharmaceutical compositions), or any combination thereof, which, in some aspects, are in combination with one or more other types of elements or components (e.g., other types of biochemical reagents, containers, packages, such as packaging intended for commercial sale, instructions of use, and the like).

VIII. Uses and Methods

VIII.A. Methods of Producing AAVs

Some aspects of the present disclosure relate to methods of producing an AAV. More specifically, in some aspects, provided herein are methods of producing a recombinant AAV comprising a transgene. In some aspects, such methods comprise transfecting a cell (e.g., host cell) with a dual helper plasmid (such as those described herein) and an expression construct (e.g., AAV construct plasmid) comprising a transgene. In some aspects, the cell is transfected with the dual helper plasmid and the expression construct concurrently. In some aspects, the cell is transfected with the dual helper plasmid and the expression construct sequentially. Unless indicated otherwise, any suitable transfection methods known in the art can be used with the present disclosure.

In some aspects, the method of producing a recombinant AAV further comprises culturing the transfected cells under suitable conditions such that the recombinant AAVs are produced. In some aspects, the method further comprises recovering the produced recombinant AAV.

The methods of producing recombinant AAVs described herein provide certain distinct benefits. As further described elsewhere in the present disclosure, the more traditional methods of producing an AAV require triple transfection, in which a host cell is transfected with the following three separate plasmids: i) a Rep-Cap plasmid including a gene encoding Rep protein and Cap protein; ii) a helper plasmid including a gene encoding the proteins (E2a, E4) and VA RNAs of adenovirus; and iii) an AAV construct plasmid for transgene expression. The recombinant AAV is only produced where the cells are successfully transfected with all of the above-mentioned three plasmids (i.e., each of the genes are taken up and delivered to the nucleus of the cells, and subsequently transcribed, replicated, and/or translated within the cells). Because of the complexity involved, such methods requiring triple transfection can result in low yield and/or be more labor intensive and costly.

Compared to such approaches, the methods of producing a recombinant AAV provided herein can result in greater yield of the recombinant AAVs. In some aspects, compared to methods requiring triple transfection (i.e., "reference method"), the amount of recombinant AAV produced is increased by at least about 10%, at least about 20%, at least about 30%, at least about 40%, at least about 50%, at least about 60%, at least about 70%, at least about 80%, at least about 90%, at least about 100% or more. In some aspects, compared to the reference cells, cells of the present disclosure are capable of increasing the amount of recombinant AAV produced by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 75-fold, or at least about 100-fold or more.

As further described elsewhere in the present disclosure, in some aspects, the methods of producing a recombinant AAV provided herein can result in reduced production and/or purification time. Additional benefits are described elsewhere in the present disclosure.

VIII.B. Methods of Producing Protein

Also disclosed herein are methods of producing a protein (or polypeptide) encoded by a transgene. In some aspects, such a method comprises culturing a cell described herein (e.g., transfected with a recombinant AAV delivery vector comprising a transgene) under suitable conditions and recovering the encoded protein. In some aspects, a method of producing a protein encoded by a transgene comprises administering a recombinant AAV to a subject in need thereof, such that the encoded polypeptide is produced in the subject. Additional disclosure relating to such in vivo method of producing a protein is provided elsewhere in the present disclosure.

VIII.C. Therapeutic Uses

In some aspects, the present disclosure further provides a use of a recombinant AAV produced using the dual helper plasmids of the present disclosure for various therapeutic applications.

For instance, in some aspects, the present disclosure provides a method for treating a disease in a subject in need thereof, comprising administering to the subject a recombinant AAV comprising a transgene and produced as described herein. In some aspects, a method of treating a disease provided herein comprises administering to a subject in need thereof any of the modified cells described herein (e.g., transfected with the recombinant AAV gene delivery vector comprising a transgene). In some aspects, a method of treating a disease provided herein comprises administering to a subject in need thereof any of the pharmaceutical compositions described herein (e.g., comprising the recombinant AAV provided herein). As is apparent from the present disclosure, the above methods can be used to treat and/or prevent any disease of interest, e.g., by modifying the transgene.

The disease to be prevented, alleviated, or treated by the present disclosure is not limited but includes all diseases that require reduced number of a drug administration. Non-limiting examples of such diseases include ophthalmic diseases and neurological diseases. In some aspects, ophthalmic diseases comprise diabetic retinopathy, choroidal neovascularization, macular degeneration, retinal degeneration, macular edema, retinal edema, macular dementia, or a combination thereof. In some aspects, neurological diseases comprise those that affect the central nervous system, the peripheral nervous system, or both. Non-limiting examples of neurological diseases include: anxiety, depression, post-traumatic stress disorder (PTSD), bipolar disorder, attention deficit hyperactivity disorder (ADHD), autism, schizophrenia, neuropathic pain, glaucoma, toxicosis, arachnoid cyst, catatonia, encephalitis, epilepsy/seizure, locked-in syndrome, meningitis, migraine, multiple sclerosis, myelopathy, Alzheimer's disease, Huntington's disease, Parkinson's disease, amyotrophic lateral sclerosis (ALS), Batten disease, Tourette's syndrome, traumatic brain injury, cerebrospinal injury, stroke, tremor (essential or Parkinsonian), dystonia, intellectual disability, brain tumor or a combination thereof.

Some aspects of the present disclosure relate to gene therapy agent that can achieve continuous expression of a transgene or a method using such agents for treating a disease.

Use of a gene delivery system provided herein (e.g., recombinant AAVs comprising a transgene) allows administration of the therapeutic agent (e.g., recombinant AAVs comprising the transgene) at intervals that can significantly reduce the number of drug administration for the convenience of physicians, patients or subjects. For instance, in some aspects, the therapeutic agent can be administered at intervals of about 1 week, about 2 weeks, about 3 weeks, about 1 month, about 2 months, about 3 months, about 4 months, about 5 months, about 6 months, about 7 months, about 8 months, about 9 months, about 10 months, about 11 months, or about 1 year or more. In some aspects, the interval is about 2 to about 3 months. In some aspects, the interval is about 6 months. In some aspects, the interval is about 1 year. In some aspects, the interval is at least about 1 year. In some aspects, depending on the symptoms of a patient, the administration can be made about 2 or 3 times with an interval of about 1-2 weeks in the early stage, followed by administration with an interval of about 2-3 months, about 6 months, or about 1 year or longer, if necessary.

In any of the methods provided herein comprising an administration step (e.g., administering any of the AAVs, cells, and/or pharmaceutical compositions described herein to a subject in need thereof), the therapeutic agent can be administered to the subject orally or parenterally. In some aspects, the therapeutic agent (e.g., any of the AAVs, cells, and/or pharmaceutical compositions described herein) is administered to the subject parenterally. Non-limited examples of parenteral administration include: intravenous injection, transdermal administration, subcutaneous injection, intramuscular injection, intravitreal injection, subretinal injection, suprachoroidal injection, eye drop administration, intracerebroventricular injection, intrathecal injection, intraamniotic injection, intraarterial injection, intraarticular injection, intracardiac injection, intracavernous injection, intracerebral injection, intracisternal injection, intracoronary injection, intracranial injection, intradural injection, epidural injection, intrahippocampal injection, intranasal injection, intraosseous injection, intraperitoneal injection, intrapleural injection, intraspinal injection, intrathoracic injection, intrathymic injection, intrauterine injection, intravaginal injection, intraventricular injection, intravesical injection, subconjunctival injection, intratum oral injection, topical injection, intraperitoneal injection, and combinations thereof.

As will be apparent to those skilled in the arts, appropriate administration dosage of a therapeutic agent (e.g., the pharmaceutical composition of the present disclosure) can vary depending on factors, such as, formulation method, mode of administration, the age, body weight, sex, pathological condition and diet of a patient, administration time, administration route, excretion rate and response sensitivity. In some aspects, a daily administration dosage of a therapeutic agent (e.g., the pharmaceutical composition of the present disclosure) is about 0.00001-100 mg/kg.

Hereinafter, the present disclosure is described in further detail through examples. The following examples are only for illustrating the present disclosure more specifically, and it will be obvious to those having ordinary knowledge in the art that the scope of the present disclosure is not limited by the examples.

EXAMPLES

Materials and Methods

Example 1 Preparation of pUC-R2C2, 5, 8 and 9 Constructs for Triple Transfection Example 1-1 Preparation of pRC8 Construct A cap8 gene fragment was obtained by conducting polymerase chain reaction (hereinafter, PCR) using pIDT-Cap8-Kan (Integrated DNA Technologies, USA) as a template and using a combination of oligo #001/002, and a plasmid backbone DNA fragment including the rep2 gene was obtained by conducting PCR using pRC6 (Takara Bio, Japan) as a template and using a combination of oligo

003/004. A pRC8 construct was prepared by joining the two DNA fragments through Gibson Assembly® (NEB, USA, Cat. No. E2611).

Example 1-2 Preparation of pUC-R2C8 Construct

A plasmid backbone was obtained by conducting PCR using pUC57-WPRE (GenScript, USA) as a template and using a combination of oligo #005/006, and a cap8 gene fragment and a rep2 gene fragment were obtained by conducting PCR using the pRC8 construct of Example 1-1 as a template and using oligo #007/008 and oligo #009/004, respectively. A pUC-R2C8 construct was prepared by joining the three DNA fragments through Gibson Assembly®.

Example 1-3 Preparation of pRC2 Construct

A cap2 gene fragment was obtained by conducting PCR using pRC2-mi342 (Takara Bio, Japan) as a template and using a combination of oligo #007/010, and a plasmid backbone fragment including the rep2 gene was obtained by conducting PCR using pRC6 (Takara Bio, Japan) as a template and using a combination of oligo #003/004. A pRC2 construct was prepared by joining the two DNA fragments through Gibson Assembly®.

Example 1-4 Preparation of pUC-R2C2 Construct

A plasmid backbone fragment including the rep2 gene was obtained by conducting PCR using the pUC-R2C8 construct of Example 1-2 as a template and using a combination of oligo #011/012, and a cap2 gene fragment was obtained by conducting PCR using the pRC2 construct of Example 1-3 as a template and using a combination of oligo #013/014. A pUC-R2C2 construct was prepared by joining the two DNA fragments through Gibson Assembly®.

Example 1-5 Preparation of pRC9 Construct

A cap9 gene fragment was obtained by conducting PCR using pIDT-Cap9-Kan (Integrated DNA Technologies, USA) as a template and using a combination of oligo #001/015, and a plasmid backbone fragment including the rep2 gene was obtained by conducting PCR using pRC6 (Takara Bio, Japan) as a template and using a combination of oligo #003/004. A pRC9 construct was prepared by joining the two DNA fragments through Gibson Assembly® (NEB, USA, Cat. No. E2611).

Example 1-6 Preparation of pUC-R2C9 Construct

A plasmid backbone was obtained by conducting PCR using pUC57-WPRE (GenScript, USA) as a template and using a combination of oligo #005/006 combination, and a cap9 gene fragment and a rep2 gene fragment were obtained by conducting PCR using the pRC9 construct of Example 1-5 as a template and using oligo #007/008, and using the pRC8 construct of Example 1-1 as a template and using oligo #009/004, respectively. A pUC-R2C9 construct was prepared by joining the three DNA fragments through Gibson Assembly®.

Example 1-7 Preparation of pUC-R2C5 Construct

A plasmid backbone was obtained by conducting PCR using pUC57-WPRE (GenScript, USA) as a template and using a combination of oligo #005/006, and a rep2-cap5 gene fragment was obtained by conducting PCR using a pRC5 construct (Takara Bio, Japan) as a template and using oligo #008/009. A pUC-R2C5 construct was prepared by joining the two DNA fragments through Gibson Assembly®.

Example 2 Preparation of pHION8 Series Constructs

Example 2-1 Preparation of pHelper-NG Construct

A pHelper-NG was prepared through cloning by joining VA-E4-pUC (GeneScript, USA) and E2a-pUC57 (GeneScript, USA) using the SalI/BamHI site shared by the two constructs (FIG. 1A). The pHelper-NG includes the E2a, E4 and VA RNA genes of adenovirus serotype 5.

Figure 1B:
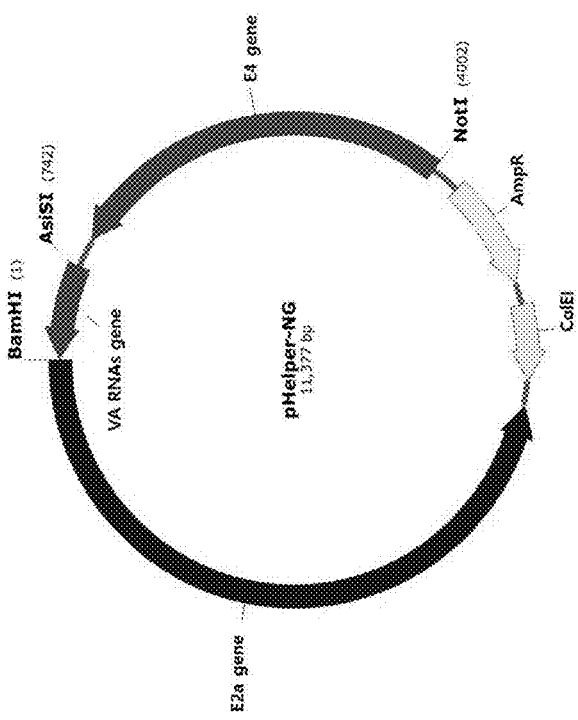
Figure 1C:
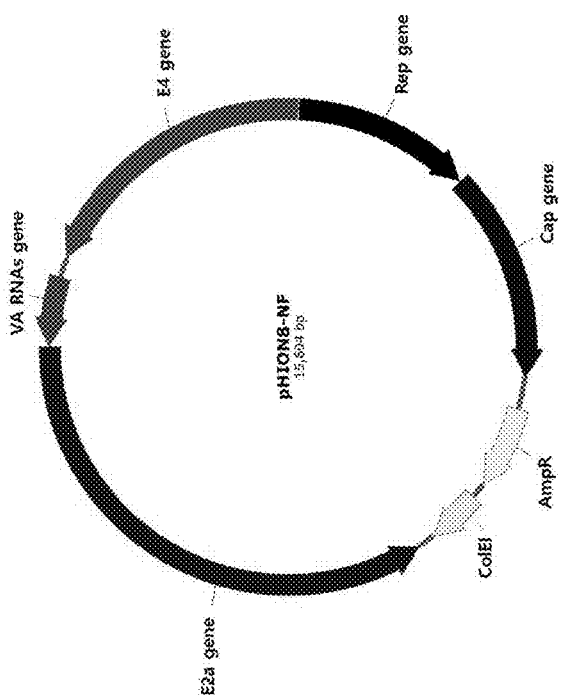

Example 2-2 Insertion of Rep2-Cap8 Gene at Different Locations of pHelper-NG Construct Example 2-2-1 Cloning of pHION8-BamHI-Forward or Reverse (pHION8-BF or -BR A rep2-cap8 gene fragment was obtained by conducting PCR using the pUC-R2C8 construct of Example 1-2 as a template and using a combination of oligo #016/017 and inserted at the BamHI site of the pHelper-NG prepared in Example 2-1 (FIGS. 1B and 1C). FIG. 1B schematically shows a pHION8-BF construct, which was prepared by inserting the rep2-cap8 gene fragment in a forward direction (clockwise direction, 5'->3') using the BamHI site present between the beginning portion of the E2a gene and the ending portion of the VA RNA gene. FIG. 1C schematically shows a pHION8-BR construct, which was prepared by inserting the rep2-cap8 construct in a reverse direction (counterclockwise direction, 3'->5') using the BamHI site present between the beginning portion of the E2a gene and the ending portion of the VA RNA gene. The pHION8-BF was named as pHNG8, and pHION8-BR as pHNGR8.

Example 2-2-2 Cloning of pHION8-NotI-Forward or -Reverse (pHION8-NF or -NR

Figure 1D:
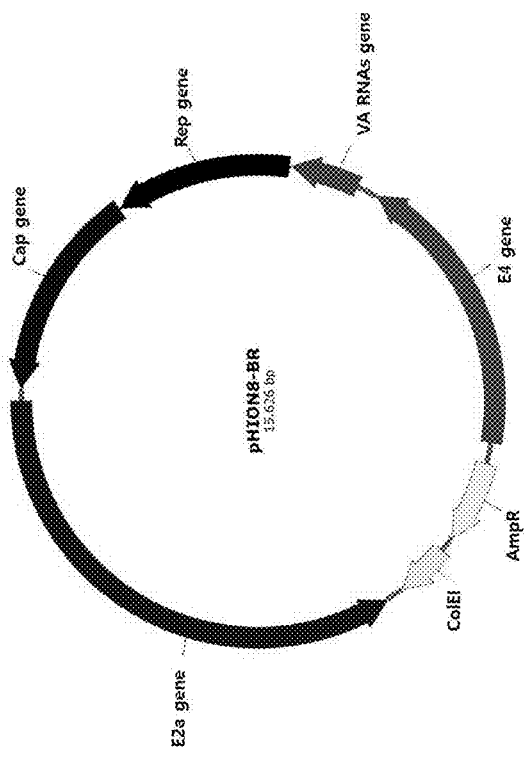
Figure 1F:
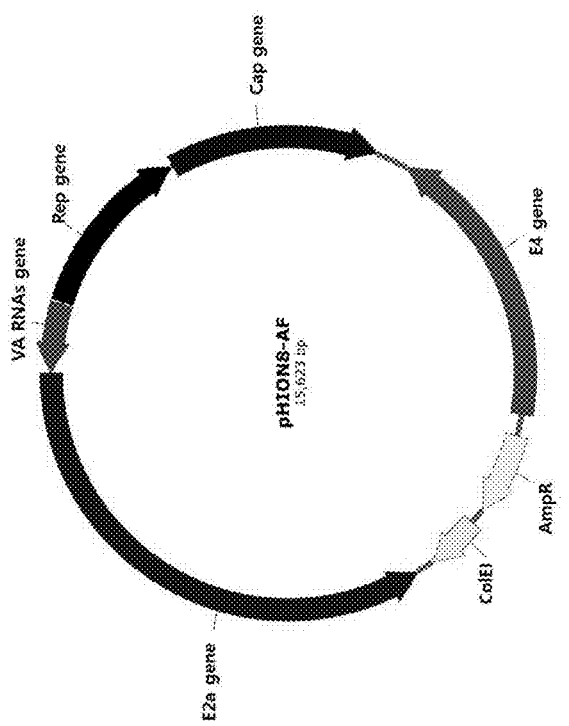
Figure 1E:
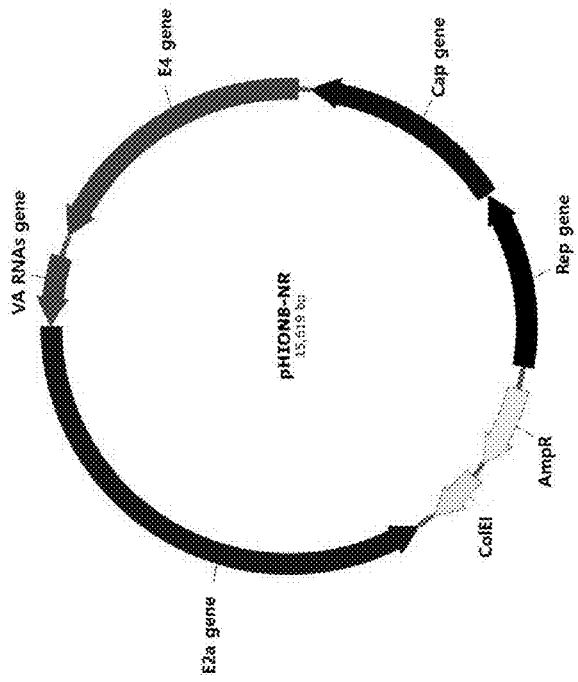

A rep2-cap8 gene fragment was obtained by conducting PCR using the pUC-R2C8 construct of Example 1-2 as a template and using a combination of oligo #018/019 and inserted at the NotI site of the pHelper-NG prepared in Example 2-1 (FIGS. 1D and 1E). FIG. 1D schematically shows a pHION8-NF construct, which was prepared by inserting the rep2-cap8 gene fragment in a forward direction (clockwise direction) using the NotI site present between the beginning portion of the E4 gene and the beginning portion of the AmpR gene. FIG. 1E schematically shows a pHION8-NR construct, which was prepared by inserting the rep2-cap8 gene fragment in a reverse direction (counterclockwise direction) using the NotI site present between the beginning portion of the E4 gene and the beginning portion of the AmpR gene.

Example 2-2-3 Cloning of pHION8-AsiSI-Forward (pHION8-AF

A pHION8-AF construct was prepared by obtaining a rep2-cap8 gene fragment by conducting PCR using the pUC-R2C8 construct of Example 1-2 as a template and using a combination of oligo #020/021 and inserting in a forward direction (clockwise direction) at the AsiSI site of the pHelper-NG prepared in Example 2-1 between the VA RNA gene and the E4 gene (FIG. 1F).

Example 3 Preparation of pHNG2, pHNG5K and pHNG9 Constructs

Example 3-1 Preparation of pHNG2 Construct

A construct prepared by obtaining a rep2-cap2 gene fragment by conducting PCR using the pUC-R2C2 construct of Example 1-4 as a template and using oligo #016/017 and inserting the same at the BamHI site of the pHelper-NG prepared in Example 2-1 was named pHNG2.

Figure 2:
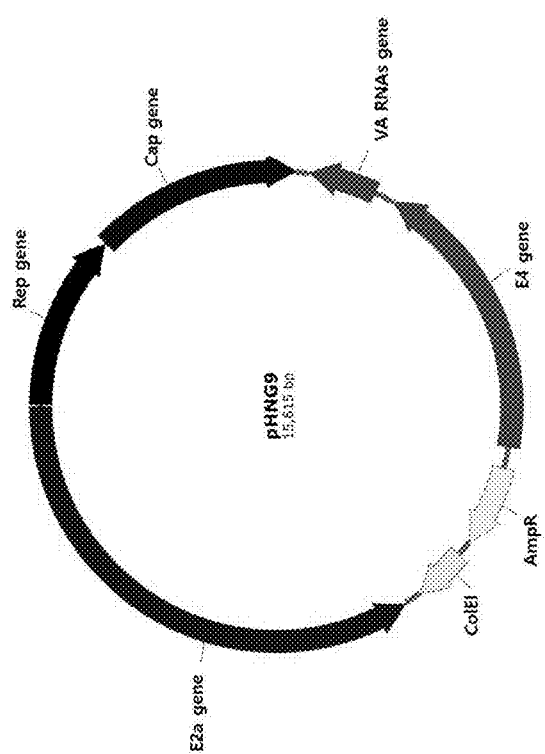
FIG. 2 shows the cleavage map of a pHNG2 construct, which is a dual helper plasmid for producing adeno-associated virus vector serotype 2 (AAV2). The pHNG2 construct was prepared by inserting a rep2-cap2 gene fragment in a forward direction using the BamHI site present between the beginning portion of the E2a gene and the ending portion of the VA RNA gene in a pHelper-NG plasmid.

FIG. 2 schematically shows the pHNG2 construct, which was prepared by inserting the rep2-cap2 gene fragment in a forward direction (clockwise direction) using the BamHI site present between the E2a gene and the VA RNA gene.

Example 3-2 Preparation of pHNG9 Construct

Figure 3:
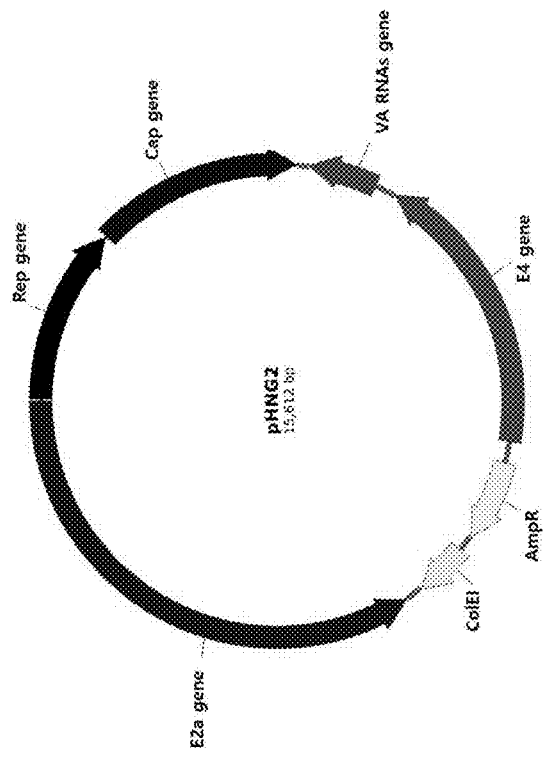
FIG. 3 shows the cleavage map of a pHNG9 construct, which is a dual helper plasmid for producing adeno-associated virus vector serotype 9 (AAV9). The pHNG9 construct was prepared by cloning a rep2-cap9 gene fragment in a forward direction using the BamHI site present between the beginning portion of the E2a gene and the ending portion of the VA RNA gene for double transfection.

A construct prepared by obtaining a rep2-cap9 gene fragment by conducting PCR using the pUC-R2C9 construct of Example 1-6 as a template and using oligo #016/#017 and inserting the same at the BamHI site of the pHelper-NG prepared in Example 2-1 was named pHNG9. FIG. 3 schematically shows the pHNG9 construct, which was prepared by inserting the rep2-cap9 gene fragment in a forward direction (clockwise direction) using the BamHI site present between the E2a gene and the VA RNA gene.

Example 3-3 Preparation of pHNG5K Construct

Example 3-3-1 Preparation of pHelper-NG-Kan Construct

A kanamycin resistance gene fragment was obtained by conducting PCR using a pMK-RQ-1-PM construct (Geneart, Thermo Fisher Scientific, USA) as a template and using a combination of oligo #018/019, and an E4 gene fragment, a fragment from VA RNAs gene to an N-term of the E2a gene and a fragment from a C-term of the E2a gene to Origin were obtained by conducting PCR using the pHelper-NG construct of Example 2-1 as a template and using oligo #020/021, oligo #022/023 and oligo #024/025, respectively. A pHelper-NG-Kan construct was prepared by joining the four DNA fragments through Gibson Assembly®.

Example 3-3-2 Insertion of Rep2-Cap5 Gene into pHelper-NG-Kan Construct

Figure 4:
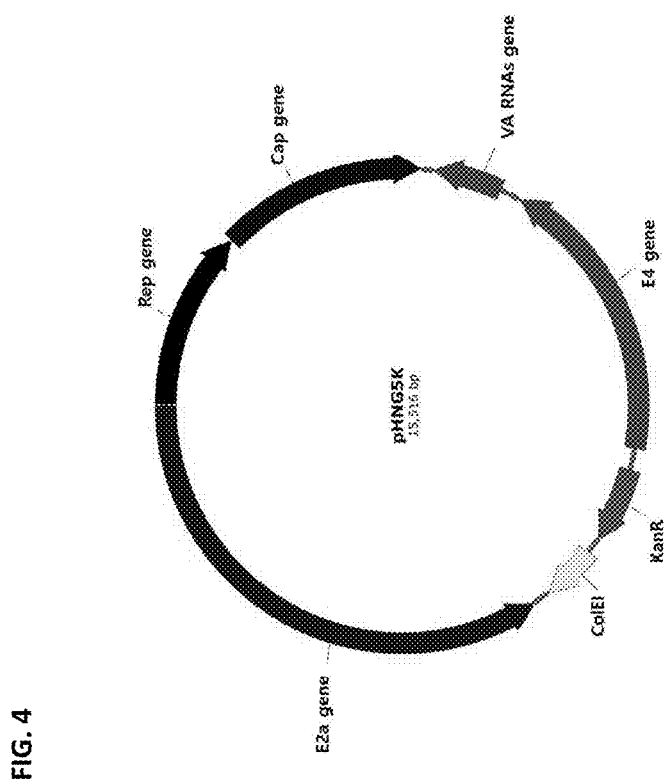
FIG. 4 shows the cleavage map of a pHNG5K construct, which is a dual helper plasmid for producing adeno-associated virus vector serotype 5 (AAV5). The pHNG5K construct was prepared by cloning a rep2-cap5 gene fragment in a forward direction using the BamHI site present between the beginning portion of the E2a gene and the ending portion of the VA RNA gene for double transfection.

A construct prepared by obtaining a rep2-cap5 gene fragment by conducting PCR using the pUC-R2C5 construct of Example 1-7 as a template and using oligo #016/#017 and inserting the same at the BamHI site of the pHelper-NG-Kan prepared in Example 3-3-1 was named pHNG5K (K denotes that a kanamycin resistance gene was used as an antibiotic resistance gene). FIG. 4 schematically shows the pHNG5K construct, which was prepared by inserting the rep2-cap5 gene fragment in a forward direction (clockwise direction) using the BamHI site present between the Eta gene and the VA RNA gene.

The sequences of the oligos used to prepare the above-described constructs are shown in Table 1:

TABLE 1

| Oligo ID (#) | SEQ ID (#) | Sequence (5' -> 3') |
|---|---|---|
| 001 | 1 | TGAACAATAAATGATTTAAATCAGGTATGGCTGCCGATGGTTATCTTCCAG |
| 002 | 2 | TAACAAGCAATTACAGATTACGGGTGAGGTAACGGG |
| 003 | 3 | TAATCTGTAATTGCTTGTTAATCAATAAACCGTTTAATTCGTTTCAG |
| 004 | 4 | TTTAAATCATTTATTGTTCAAAGATGCAGTCATCCAAATCCAC |
| 005 | 5 | ATTAACTACAAGCTGTTTCCTGTGTGAAATTGTTATCC |
| 006 | 6 | GCGGCTGCGCTTAAGCCAGCCCCGACACC |
| 007 | 7 | TGAACAATAAATGATTTAAATCAGGTATGGCTGCCG |
| 008 | 8 | GGAAACAGCTTGTAGTTAATGATTAACCCGCCATGC |
| 009 | 9 | GCTGGCTTAAGCGCAGCCGCCATG |
| 010 | 10 | TAACAAGCAATTACAGATTACGAGTCAGGTATCTGG |
| 011 | 11 | GGTCGCTGGGGACCTTAATC |
| 012 | 12 | CCATGGCTACGTAGATAAGTAGCATG |
| 013 | 13 | GATTAAGGTCCCCAGCGACC |
| 014 | 14 | ACTTATCTACGTAGCCATGGAAACTAGATAAGAAAGAAATACG |
| 015 | 15 | TAACAAGCAATTACAGATTACGAGTCAGGTATCTGGTGC |
| 016 | 16 | GGAAGATCTTTAAGCGCAGCCGCCATG |
| 017 | 17 | GGAAGATCTTGTAGTTAATGATTAACCCGCCATGC |
| 018 | 18 | GGCACTTTTCGGGGAAATGTG |
| 019 | 19 | CAATCTAAAGTATATATGAGTAAACTTGGTCTGACAG |
| 020 | 20 | ATGATACCCTTGCGAATTTATCCACC |
| 021 | 21 | CACATTTCCCCGAAAAGTGCC |
| 022 | 22 | GGTGGATAAATTCGCAAGGGTATCAT |
| 023 | 23 | ACCTATCACATCTTTTTCCAAAACTGC |
| 024 | 24 | GCAGTTTTGGAAAAAGATGTGATAGGT |
| 025 | 25 | CTGTCAGACCAAGTTTACTCATATATACTTTAGATTG |
| 026 | 26 | GCCAGCCATCTGTTGT |
| 027 | 27 | GGAGTGGCACCTTCCA |
| 028 | 28 | FAM-TCCCCCGTGCCTTCCTTGACC-BHQ1 |

And, constructs prepared by inserting the rep-cap gene fragment between the E2a gene and the VA RNA gene in a forward direction (clockwise direction, 5'->3') were collectively named pHNG (pHNG2, pHNG5 (including pHNG5K), pHNG8, pHNG9, etc.) and constructs prepared by inserting in a reverse direction (counterclockwise direction, 3'->5') were collectively named pHNGR (pHNGR8, etc.). Their cleavage maps are shown in FIGS. 5A and 5B.

Example 4 Preparation of AAV Construct Plasmid Including Transgene

An AAV construct plasmid including a transgene was prepared according to the method described in Korean Patent Application No. 10-2020-0084038. Specifically, the plasmid was prepared from a pUC57 plasmid, with AAV2 ITR (inverted terminal repeat) base sequences necessary for AAV capsid packaging on both sides and a CMV enhancer, a chicken β-actin promoter, a hybrid intron, an eGFP gene as a transgene, a WPRE sequence, four repeating miR142-3p target sequences and the pA sequence of bovine growth hormone included there between.

Example 5 Base Sequencing

The base sequences of all the constructs prepared above were confirmed through base sequencing (DNA sequencing) (Bionics, Korea).

Example 6 Cell Culture

HEK293 cells were wet-cultured using an MEM medium (Gibco, USA, Cat. No. 42360-032) containing 10% FBS (fetal bovine serum, Gibco, USA, Cat. No. 16000-044) and 1% penicillin-streptomycin (Gibco, USA, Cat. No. 15140-163) under the condition of 5% $CO_2$ and 37° C. Expi293 cells were wet-cultured using an Expi293 medium (Gibco, USA, Cat. No. A14351-01) supplemented with 1% penicillin-streptomycin under the condition of 8% $CO_2$ and 37° C. while shaking at 250 rpm.

Example 7 Transfection

Example 7-1 Transfection of Adhesion Cells for Production of AAV

For transfection, HEK293 cells were washed twice using DPBS (Gibco, USA, Cat. No. 14190-250), detached from the culture dish by treating with trypsin-EDTA (Gibco, USA, Cat. No. 25200-114), and then inoculated onto a 150-mm culture dish at $2 \times 10^7$ cell/dish. After culturing for 24 hours, a pHelper-NG plasmid, a pUC-R2C2, pUC-R2C8 or pUC-R2C9 plasmid and an AAV construct plasmid including the transgene, 3.73 pmol each, were dissolved in 500 μL of Opti-MEM (Gibco, USA, Cat. No. 51985-034) for triple transfection. For double transfection, a pHION8 plasmid and an AAV construct plasmid including the transgene, 3.73 pmol each, were dissolved in 500 μL of Opti-MEM (Gibco, USA, Cat. No. 51985-034). Then, after diluting polyethylenimine (PEI, Polyscience, USA, Cat. No. 23966-1) corresponding to 2-fold of the total DNAs in 500 μL of Opti-MEM, the two solutions were mixed immediately to prepare a transfection solution. After incubating at room temperature for 30 minutes, 1 mL of the transfection solution was added to the culture dish on which the HEK293 cells were being cultured.

Example 7-2 Transfection of Suspension Cells for Production of AAV

For production of AAV, $6 \times 10^8$ cells were inoculated to 220 mL of an Expi293 medium in a 1-L Erlenmeyer culture flask. After culturing for about 3-4 hours for stabilization, a pHelper-NG plasmid, a pUC-R2C2, pUC-R2C5, pUC-R2C8 or pUC-R2C9 plasmid and an AAV construct plasmid including the transgene, 3.73 pmol each, were dissolved in 10 mL of Opti-MEM (Gibco, USA, Cat. No. 51985-034) for triple transfection. For double transfection, a pHION8 plasmid, a pHNG2 plasmid or a pHNG9 plasmid and an AAV construct plasmid including the transgene, 3.73 pmol each, were dissolved in 10 mL of Opti-MEM (Gibco, USA, Cat. No. 51985-034). Then, after diluting polyethylenimine (PEI, Polyscience, USA, Cat. No. 23966-1) corresponding to 2-fold of the total DNAs in 10 mL of Opti-MEM, the two solutions were mixed immediately to prepare a transfection solution. After incubating at room temperature for 30 minutes, 20 mL of the transfection solution was added to the culture flask.

Example 8 Purification of AAV

After conducting transfection for 72 hours in Example 7-1 or 7-2, the cells were incubated for 3 hours after adding NaCl to the culture dish and the culture flask to a concentration of 500 mM (salt shock). Then, after recovering all the culture and removing debris through centrifugation, centrifugation was performed using Centricon (Vivaspin 20, 100,000 MWCO PES, Sartorius, Germany) having a molecular weight cut-off pore size of 100 kDa at 4° C. and 4000 rpm until about 200 μL of a supernatant remained. Then, the supernatant containing a recombinant adeno-associated virus vector was recovered and used for experiment or stored at −80° C.

Example 9 Determination of AAV Titer qPCR (Bio-Rad, USA, CFX96) was conducted to determine the titer of the AAV purified in Example 8. The AAV was treated with DNaseI at 37° C. for 1 hour using a DNaseI reaction buffer (New England Biolab, USA, M0303S). Then, after treating the DNaseI-treated sample with proteinase K (Invitrogen, USA, Cat. No. AM2548) at 55° C. for 30 minutes, the proteinase K was inactivated by incubating at 95° C. for 15 minutes. The prepared sample was used as a template for qPCR, the AAV construct plasmid ($7.4 \times 10^8$ to $7.4 \times 10^4$, 10-fold dilution) was used to obtain a standard curve, and a recombinant adeno-associated virus 2 reference standard stock (rAAV2-RSS, ATCC, USA, Cat. No. VR-1616) or a recombinant adeno-associated virus 8 reference standard stock (rAAV8-RSS, ATCC, USA, Cat. No. VR-1816) was used as a positive control group. For qPCR for determining the titer, 2×SsoAdvanced Universal Probe Supermix (Bio-Rad, USA, Cat. No. 172-5282) and bGH poly A sequence-specific primers/probe set (#026, #027 and #028) were used. The qPCR was repeated for 40 cycles of denaturation at 95° C. for 10 minutes, followed by 95° C. for 30 seconds and 60° C. for 1 minute. The Bio-Rad CFX Maestro 1.1 software (Bio-Rad, USA) was used for analysis of the standard curve and quantification.

Example 10 Transfection Using Adeno-Associated Virus Vector In Vitro

For transfection of the adeno-associated virus vector, HEK293 cells were inoculated on a 24-well culture plate with $4 \times 10^5$ cells per well. 24 hours later, each well was treated with 5 μM MG132 (Sigma-Aldrich, USA, Cat. No. M7449) for 8 hours. The cells were treated with 2,500 MOI (multiplicity of infection) of AAV2, or with 10,000 MOI of AAV8 or AAV9, and then cultured for 72 hours.

Example 11 Measurement of Expression Level of eGFP Gene Through Flow Cytometry

The expression of eGFP was measured by flow cytometry (Beckman Coulter, USA, CytoFlex). After transfection for 72 hours, the cells were treated with DPBS and detached using trypsin. After centrifuging the cells at 1500 rpm for 5 minutes, the cells were resuspended by adding 500 µL of DPBS supplemented with 2% FBS. The single cell region was distinguished from the FSC vs SSC plot and the expression level of FL1-A (green) was measured. The result of flow cytometry was analyzed using the FlowJo software 10.5.3 (Becton Dickinson & Company, USA).

Example 12 Statistical Analysis

All experiments were repeated 3 or more times. Comparison between two groups was performed by Student's t-test using the Prism software 8.1.1 (GraphPad Software, Inc., USA), and comparison of three or more groups was performed by one-way ANOVA and Tukey's multiple comparisons test. * indicates p<0.05, indicates p<0.01 and *indicates p<0.001.
Experimental Results
1. Selection of Helper-In-One Plasmid Construct Showing Increased AAV8 Production
1-1. Effect of Triple Transfection and Double Transfection using pHION8 Series on Increased or Decreased AAV8 Production in Adhesion Cells (HEK293)

Figure 6:
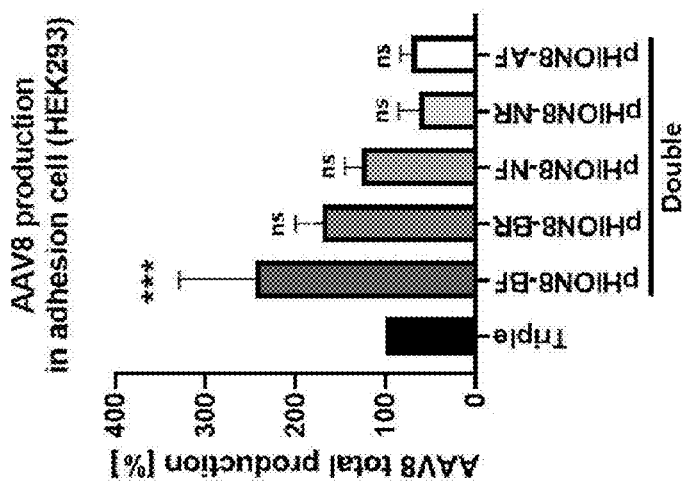
FIG. 6 shows a result of observing the effect of double transfection (Double) using pHION8 series on the increase or decrease of AAV8 production in adhesion cells (HEK293) as compared to triple transfection (Triple).

The effect of the location of the rep2-cap8 gene in the five Helper-In-One plasmid constructs used for double transfection (pHION8 series; pHION8-BF, pHION8-BR, pHION8-NF, pHION8-NR and pHION8-AF) on AAV8 production in adhesion cells (HEK293) was tested. Different results in AAV8 production were observed depending on the location of the rep2-cap8 gene for double transfection with respect to AAV8 production by triple transfection as 100%. The AAV8 production was increased to 244.3% when the pHION8-BF construct (pHNG8) was used and to 170.2% when the pHION8-BR construct (pHNGR8) was used. When the pHION8-NF construct was used, the production was increased to 126.0%, but the increase was not statistically significant (p=0.82). In contrast, the AAV8 production was decreased when the pHION8-NR or pHION8-AF construct was used (62.4% (p=0.50), 71.7% (p=0.77)) (FIG. 6).
1-2. Effect of Triple Transfection and Double Transfection using pHION8 Series on Increased or Decreased AAV8 Production in Suspension Cells (Expi293)

Figure 7:
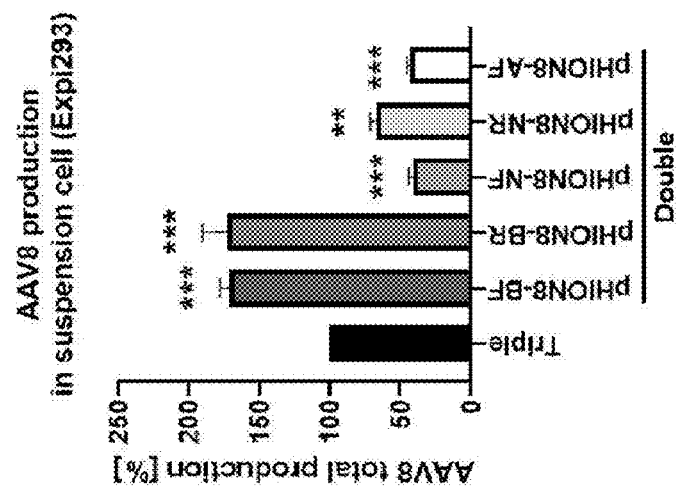
FIG. 7 shows a result of observing the effect of double transfection (Double) using pHION8 series on the increase or decrease of AAV8 production in suspension cells (Expi293) as compared to triple transfection (Triple).

The same experiment as 1-1 was tested for suspension cells (Expi293F). Similarly to the adhesion cells, the AAV8 production was increased statistically significantly to 177.1% (p<0.001) when the pHION8-BF construct was used and to 173.1% (p<0.001) when the pHION8-BR construct was used, for double transfection, as compared to triple transfection. However, when the pHION8-NF, pHION8-NR and pHION8-AF constructs were used, the production was decreased statistically significantly to 40.9%, 66.7% and 43.1%, respectively (FIG. 7).

These results suggest that the AAV production can vary depending on the relative location and direction of the rep2-cap8 gene in the dual helper plasmid. Hereinafter, the construct wherein the rep2-cap gene is present in a forward direction (BF) at the BamHI site in the pHION plasmid for double transfection is named pHNG, and the construct wherein it is present in a reverse direction (BR) is named pHNGR. The number that follows indicates the serotype of the adeno-associated virus from which the cap gene is derived (pHION8-BF=pHNG8, pHION8-BR=pHNGR8).
2. Increased AAV2 Production in Adhesion Cells (HEK293) by Triple Transfection and Double Transfection using pHNG2

A pHNG2 construct was prepared by inserting the rep2-cap2 gene fragment in a forward direction using the BamHI site present between the beginning portion of the E2a gene and the ending portion of the VA RNA gene in a pHelper-NG plasmid, and it was used for double transfection (FIG. 2).

Figure 8:
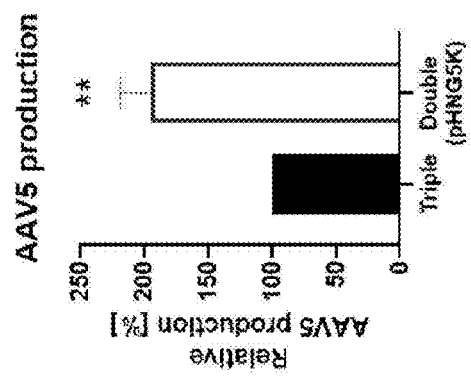
FIG. 8 shows a result of observing the effect of double transfection (Double) using pHNG2 on the increase of AAV2 production in adhesion cells (HEK293) as compared to triple transfection (Triple).

When AAV2 production was compared for triple transfection and double transfection using the pHNG2, the AAV2 production was increased significantly to 279.6% (p<0.001) for the double transfection as compared to the triple transfection (FIG. 8). Similarly to the increased AAV8 production by double transfection using pHNG8, this result suggests that AAV2 production by double transfection can be increased by locating the rep2-cap2 gene between the beginning portion of the E2a gene and the ending portion of the VA RNA gene.
3. Increased AAV9 Production by Double Transfection using pHNG9 in Adhesion Cells (HEK293)

For double transfection, a pHNG9 construct was prepared by cloning the rep2-cap9 gene fragment in a forward direction using the BamHI site present between the beginning portion of the E2a gene and the ending portion of the VA RNA gene (FIG. 3).

Figure 9:
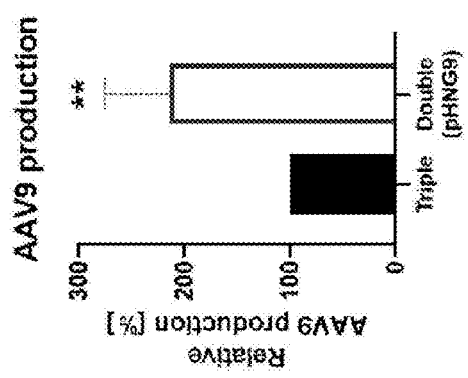
FIG. 9 shows a result of observing the effect of double transfection (Double) using pHNG9 on the increase of AAV9 production in adhesion cells (HEK293) as compared to triple transfection (Triple).

As a result of comparing AAV9 production by triple transfection and double transfection using pHNG9, it was confirmed that the AAV9 production was significantly increased to 214.0% (p<0.001) by the double transfection as compared to the triple transfection (FIG. 9). This result was consistent to the increased AAV8 or AAV2 production by double transfection using pHNG8 and pHNG2. In conclusion, this suggests that the production of adeno-associated virus serotype 9 (AAV9) by double transfection can also be increased by locating the rep2-cap gene between the beginning portion of the E2a gene and the ending portion of the VA RNA gene.
4. Increased AAV5 Production by Double Transfection Using pHNG5K in Adhesion Cells (HEK293)

For double transfection, a pHNG5K construct was prepared by cloning the rep2-cap5 gene fragment in a forward direction using the BamHI site present between the beginning portion of the E2a gene and the ending portion of the VA RNA gene (FIG. 4).

Figure 10:
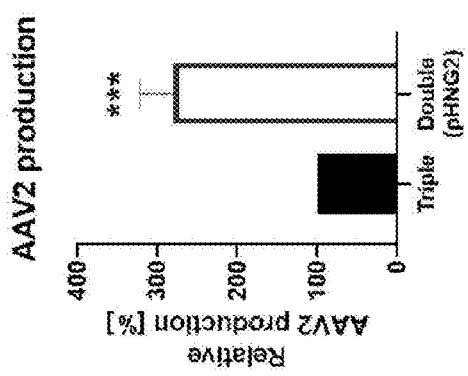
FIG. 10 shows a result of observing the effect of double transfection (Double) using pHNG5K on the increase of AAV5 production in adhesion cells (HEK293) as compared to triple transfection (Triple).

As a result of comparing AAV5 production by triple transfection and double transfection using pHNG5K, it was confirmed that the AAV5 production was significantly increased to 194.7% (p=0.002) by the double transfection as compared to the triple transfection (FIG. 10). This result was consistent to the increased AAV8, AAV2 or AAV9 production by double transfection using pHNG8, pHNG2 and pHNG9.

In conclusion, this suggests that the production of adeno-associated virus serotype 5 (AAV5) by double transfection can also be increased by locating the rep2-cap gene between the beginning portion of the E2a gene and the ending portion of the VA RNA gene.
5. Equivalence of Cell Transduction Efficiency of AAV8s Produced by Triple Transfection or Double Transfection (pHNG8 or pHNGR8 Construct)

Figure 11:
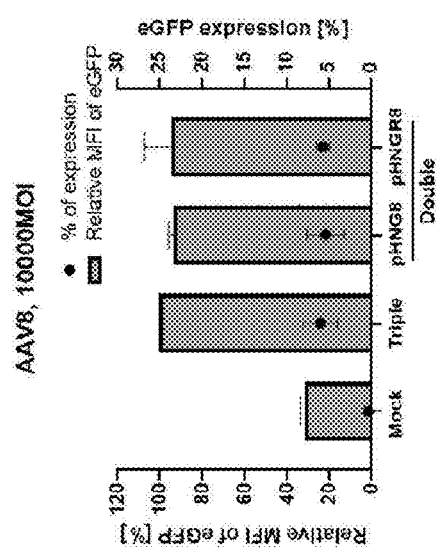
FIG. 11 shows that AAV8s produced by triple transfection (Triple) or by double transfection (Double) using Helper-In-One constructs show comparable cell transduction efficiency.

The cellular infectivity and gene expression ability of AAV8 produced by triple transfection and AAV8 produced by double transfection using pHNG8 and pHNGR8 were compared. The AAV8s were designed to express the eGFP protein. After infecting HEK293 cells with 10,000 MOI of AAV8, the expression level of eGFP in the cells was measured by flow cytometry 72 hours later. As a result, when compared with the AAV8 produced by triple transfection, the AAV8 produced by double transfection using pHNG8 and pHNGR8 showed similar cellular infectivity (Triple: 6.0%, pHNG8: 5.4%, pHNGR8: 5.7%) and also showed similar eGFP expression level (pHNG8: 93.4%, pHNGR8: 94.6%) in the cells. This result suggests that the AAV8 produced by triple transfection and the AAV8 produced by double transfection using pHNG8 and pHNGR8 have no difference in cellular infectivity and gene expression ability after infection (FIG. 11).

6. Equivalence of Transduction Efficiency of AAV2s Produced by Triple Transfection or Double Transfection (pHNG2)

Figure 12:
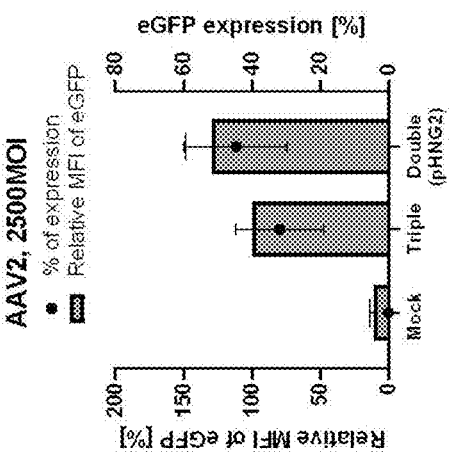
FIG. 12 shows that AAV2s produced by triple transfection (Triple) or by double transfection (Double) using a pHNG2 construct show comparable cell transduction efficiency.

In gene delivery (transduction) using AAV2, the cellular infectivity and gene expression ability of AAV2 produced by triple transfection and AAV2 produced by double transfection using pHNG2 were compared. The AAV2s were designed to express the eGFP protein. After infecting HEK293 cells with 2,500 MOI of AAV2, the proportion of cells expressing eGFP and the expression level of eGFP in the cells were measured by flow cytometry 72 hours later. As a result, when compared with the AAV2 produced by triple transfection, the AAV2 produced by double transfection using pHNG2 showed at least comparable cellular infectivity (Triple: 32.0%, BF: 44.7%; p=0.38) and also showed comparable or slightly higher eGFP expression level (129.6%, p=0.02) per infected cell. This result suggests that the AAV2 produced by double transfection using pHNG2 exhibits cellular infectivity and gene expression ability after infection at least comparable to those of the AAV2 produced by triple transfection (FIG. 12).

7. Equivalence of Transduction Efficiency of AAV9s Produced by Triple Transfection or Double Transfection (pHNG9)

Figure 13:
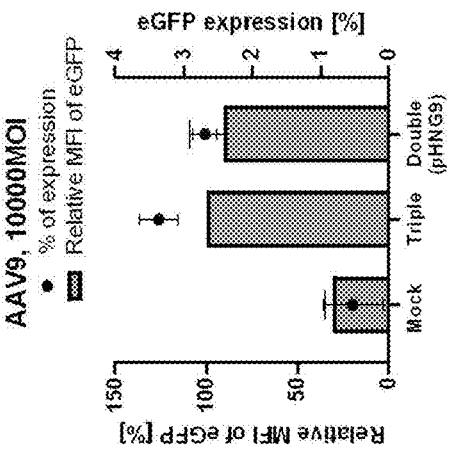
FIG. 13 shows that AAV9s produced by triple transfection (Triple) or by double transfection (Double) using a pHNG9 construct show comparable cell transduction efficiency.

In gene delivery (transduction) using AAV9, the cellular infectivity and gene expression ability of AAV9 produced by triple transfection and AAV9 produced by double transfection using pHNG9 were compared. The AAV9s were designed to express the eGFP protein. After infecting HEK293 cells with 10,000 MOI of AAV9, the expression level of eGFP in the cells was measured by flow cytometry 72 hours later. As a result, when compared with the AAV9 produced by triple transfection, the AAV9 produced by double transfection using pHNG9 showed similar eGFP expression level (90.9%, p=0.35). This result suggests that the AAV9 produced by triple transfection and the AAV9 produced by double transfection using pHNG9 have no difference in cellular infectivity and gene expression ability (FIG. 13).

Although the specific exemplary aspects of the present disclosure have been described above, those having ordinary knowledge in the art will be able to variously change and modify the present disclosure without departing from the technical idea of the present disclosure described in the claims through addition, change, deletion, etc. of elements, and such changes and modifications also belong to the scope of the present disclosure.

What is claimed is:

1. A dual helper plasmid comprising an E2a gene, E4 gene, VA RNA gene, and rep-cap gene, wherein the E2a, E4, and the VA RNA genes are linked sequentially, and wherein (i) the rep-cap gene is located between the 5'-terminal of the E2a gene and the 3'-terminal of the VA RNA gene in a clockwise direction (from 5' to 3'); or (ii) the rep-cap gene is located between the 5'-terminal of the E2a gene and the 3'-terminal of the VA RNA gene in a counterclockwise direction (from 3' to 5').

2. The dual helper plasmid of claim 1, wherein the 5'-terminal of the rep-cap gene is linked to the 5'-terminal of the E2a gene, and wherein the 3'-terminal of the rep-cap gene is linked to the 3'-terminal of the VA RNA gene.

3. The dual helper plasmid of claim 1, wherein the 3'-terminal of the rep-cap gene is linked to the 5'-terminal of the E2a gene, and wherein the 5'-terminal of the rep-cap gene is linked to the 3'-terminal of the VA RNA gene.

4. The dual helper plasmid of claim 1, wherein the rep-cap gene comprises a rep gene and a cap gene, and wherein the 3'-terminal of the rep gene is linked to the 5'-terminal of the cap gene.

5. The dual helper plasmid of claim 4, wherein the rep gene comprises a rep2 gene derived from adeno-associated virus serotype 2 (AAV2).

6. The dual helper plasmid of claim 4, wherein the cap gene comprises a cap gene derived from adeno-associated virus serotype 2 (AAV2; cap2), serotype 5 (AAV5; cap5), serotype 8 (AAV8; cap8), or serotype 9 (AAV9; cap9).

7. The dual helper plasmid of claim 1, wherein the E2a gene comprises an E2a gene derived from adenovirus serotype 5 (Ad5).

8. The dual helper plasmid of claim 1, wherein the E4 gene comprises an E4 gene derived from adenovirus serotype 5 (Ad5).

9. The dual helper plasmid of claim 1, wherein the VA RNA gene comprises a VA RNA gene derived from adenovirus serotype 5 (Ad5).

10. The dual helper plasmid of claim 1, wherein the dual helper plasmid comprises: (i) an E2a gene, which comprises the sequence set forth in SEQ ID NO: 34; (ii) an E4 gene, which comprises the sequence set forth in SEQ ID NO: 35; (iii) a VA RNA gene, which comprises the sequence set forth in SEQ ID NO: 36; (iv) a cap gene, which comprises the sequence set forth in SEQ ID NO: 30, SEQ ID NO: 31, SEQ ID NO: 32 or SEQ ID NO: 33; and (v) a rep gene, which comprises the sequence set forth in SEQ ID NO: 29.

11. A composition for producing adeno-associated virus comprising the dual helper plasmid of claim 1.

12. The composition of claim 11, which further comprises an additional plasmid.

13. The composition of claim 12, wherein the additional plasmid is an AAV construct plasmid.

14. The composition of claim 12, wherein the additional plasmid comprises: (a) an inverted terminal repeat (ITR); (b) a transgene; and (c) a control element operably linked to the transgene.

15. The composition of claim 14, wherein the control element comprises a promoter, enhancer, exon sequence, intron sequence, splicing donor or acceptor sequence, miRNA target sequence, woodchuck hepatitis virus post-transcriptional regulatory element (WPRE) sequence, polyadenylation (pA) sequence, or combinations thereof.

16. The composition of claim 14, wherein the transgene encodes a wild type polypeptide or any variant thereof, a fusion protein, an antibody or an antigen-binding fragment thereof, a RNA-based molecule, or any combination thereof.

17. An in vitro cell comprising the dual helper plasmid of claim 1.

18. A method of producing a recombinant AAV, comprising in vitro modifying a cell to comprise a first plasmid and a second plasmid, wherein the first plasmid is the dual helper plasmid of claim 1, and wherein the second plasmid comprises an AAV construct plasmid, which comprises a transgene, an inverted terminal repeat (ITR), and a control element operably linked to the transgene.

19. The method of claim 18, wherein the in vitro modifying comprises transfecting the cell with the first plasmid and the second plasmid.

20. The method of claim 18, further comprising isolating the produced recombinant AAV.

21. A method of increasing the yield of recombinant AAV during production, comprising in vitro modifying a cell to comprise a first plasmid and a second plasmid, wherein the first plasmid is the dual helper plasmid of claim 1 and the second plasmid comprises an AAV construct plasmid, which comprises a transgene, an inverted terminal repeat (ITR), and a control element operably linked to the transgene, and wherein the amount of recombinant AAV produced after the in vitro modifying is increased compared to the corresponding amount produced with a reference method, and wherein the reference method comprises modifying a corresponding cell to comprise the following three separate plasmids: (i) a Rep-Cap plasmid comprising a gene encoding Rep protein and Cap protein; (ii) a helper plasmid comprising a gene encoding the proteins (E2a, E4) and VA RNAs of adenovirus; and (iii) an AAV construct plasmid comprising a transgene.

22. The method of claim 21, wherein the amount of recombinant AAV produced is increased by at least 2-fold, as compared to the corresponding amount produced using the reference method.

23. A recombinant AAV produced by the method of claim 21.

* * * * *

SEQUENCE LISTING

```
<160> NUMBER OF SEQ ID NOS: 38

<210> SEQ ID NO 1
<211> LENGTH: 51
<212> TYPE: DNA
<213> ORGANISM: Artificial Sequence
<220> FEATURE:
<223> OTHER INFORMATION: Oligo ID NO: 001

<400> SEQUENCE: 1
tgaacaataa atgatttaaa tcaggtatgg ctgccgatgg ttatcttcca g          51

<210> SEQ ID NO 2
<211> LENGTH: 36
<212> TYPE: DNA
<213> ORGANISM: Artificial Sequence
<220> FEATURE:
<223> OTHER INFORMATION: Oligo ID NO: 002

<400> SEQUENCE: 2
taacaagcaa ttacagatta cgggtgaggt aacggg                           36

<210> SEQ ID NO 3
<211> LENGTH: 47
<212> TYPE: DNA
<213> ORGANISM: Artificial Sequence
<220> FEATURE:
<223> OTHER INFORMATION: Oligo ID NO: 003

<400> SEQUENCE: 3
taatctgtaa ttgcttgtta atcaataaac cgtttaattc gtttcag               47

<210> SEQ ID NO 4
```

<211> LENGTH: 43
<212> TYPE: DNA
<213> ORGANISM: Artificial Sequence
<220> FEATURE:
<223> OTHER INFORMATION: Oligo ID NO: 004

<400> SEQUENCE: 4
tttaaatcat ttattgttca aagatgcagt catccaaatc cac       43

<210> SEQ ID NO 5
<211> LENGTH: 38
<212> TYPE: DNA
<213> ORGANISM: Artificial Sequence
<220> FEATURE:
<223> OTHER INFORMATION: Oligo ID NO: 005

<400> SEQUENCE: 5
attaactaca agctgtttcc tgtgtgaaat tgttatcc            38

<210> SEQ ID NO 6
<211> LENGTH: 29
<212> TYPE: DNA
<213> ORGANISM: Artificial Sequence
<220> FEATURE:
<223> OTHER INFORMATION: Oligo ID NO: 006

<400> SEQUENCE: 6
gcggctgcgc ttaagccagc cccgacacc                      29

<210> SEQ ID NO 7
<211> LENGTH: 36
<212> TYPE: DNA
<213> ORGANISM: Artificial Sequence
<220> FEATURE:
<223> OTHER INFORMATION: Oligo ID NO: 007

<400> SEQUENCE: 7
tgaacaataa atgatttaaa tcaggtatgg ctgccg              36

<210> SEQ ID NO 8
<211> LENGTH: 36
<212> TYPE: DNA
<213> ORGANISM: Artificial Sequence
<220> FEATURE:
<223> OTHER INFORMATION: Oligo ID NO: 008

<400> SEQUENCE: 8
ggaaacagct tgtagttaat gattaacccg ccatgc              36

<210> SEQ ID NO 9
<211> LENGTH: 24
<212> TYPE: DNA
<213> ORGANISM: Artificial Sequence
<220> FEATURE:
<223> OTHER INFORMATION: Oligo ID NO: 009

<400> SEQUENCE: 9
gctggcttaa gcgcagccgc catg                           24

<210> SEQ ID NO 10
<211> LENGTH: 36
<212> TYPE: DNA
<213> ORGANISM: Artificial Sequence
<220> FEATURE:
<223> OTHER INFORMATION: Oligo ID NO: 010

<400> SEQUENCE: 10

```
taacaagcaa ttacagatta cgagtcaggt atctgg                              36

<210> SEQ ID NO 11
<211> LENGTH: 20
<212> TYPE: DNA
<213> ORGANISM: Artificial Sequence
<220> FEATURE:
<223> OTHER INFORMATION: Oligo ID NO: 011

<400> SEQUENCE: 11
ggtcgctggg gaccttaatc                                                20

<210> SEQ ID NO 12
<211> LENGTH: 26
<212> TYPE: DNA
<213> ORGANISM: Artificial Sequence
<220> FEATURE:
<223> OTHER INFORMATION: Oligo ID NO: 012

<400> SEQUENCE: 12
ccatggctac gtagataagt agcatg                                         26

<210> SEQ ID NO 13
<211> LENGTH: 20
<212> TYPE: DNA
<213> ORGANISM: Artificial Sequence
<220> FEATURE:
<223> OTHER INFORMATION: Oligo ID NO: 013

<400> SEQUENCE: 13
gattaaggtc cccagcgacc                                                20

<210> SEQ ID NO 14
<211> LENGTH: 43
<212> TYPE: DNA
<213> ORGANISM: Artificial Sequence
<220> FEATURE:
<223> OTHER INFORMATION: Oligo ID NO: 014

<400> SEQUENCE: 14
acttatctac gtagccatgg aaactagata agaaagaaat acg                      43

<210> SEQ ID NO 15
<211> LENGTH: 39
<212> TYPE: DNA
<213> ORGANISM: Artificial Sequence
<220> FEATURE:
<223> OTHER INFORMATION: Oligo ID NO: 015

<400> SEQUENCE: 15
taacaagcaa ttacagatta cgagtcaggt atctggtgc                           39

<210> SEQ ID NO 16
<211> LENGTH: 27
<212> TYPE: DNA
<213> ORGANISM: Artificial Sequence
<220> FEATURE:
<223> OTHER INFORMATION: Oligo ID NO: 016

<400> SEQUENCE: 16
ggaagatctt taagcgcagc cgccatg                                        27

<210> SEQ ID NO 17
<211> LENGTH: 35
<212> TYPE: DNA
```

```
<213> ORGANISM: Artificial Sequence
<220> FEATURE:
<223> OTHER INFORMATION: Oligo ID NO: 017

<400> SEQUENCE: 17
ggaagatctt gtagttaatg attaacccgc catgc                                35

<210> SEQ ID NO 18
<211> LENGTH: 21
<212> TYPE: DNA
<213> ORGANISM: Artificial Sequence
<220> FEATURE:
<223> OTHER INFORMATION: Oligo ID NO: 018

<400> SEQUENCE: 18 ggcactttc ggggaaatgt g                                                21

<210> SEQ ID NO 19
<211> LENGTH: 37
<212> TYPE: DNA
<213> ORGANISM: Artificial Sequence
<220> FEATURE:
<223> OTHER INFORMATION: Oligo ID NO: 019

<400> SEQUENCE: 19
caatctaaag tatatatgag taaacttggt ctgacag                              37

<210> SEQ ID NO 20
<211> LENGTH: 26
<212> TYPE: DNA
<213> ORGANISM: Artificial Sequence
<220> FEATURE:
<223> OTHER INFORMATION: Oligo ID NO: 020

<400> SEQUENCE: 20
atgataccct tgcgaattta tccacc                                          26

<210> SEQ ID NO 21
<211> LENGTH: 21
<212> TYPE: DNA
<213> ORGANISM: Artificial Sequence
<220> FEATURE:
<223> OTHER INFORMATION: Oligo ID NO: 021

<400> SEQUENCE: 21
cacatttccc cgaaaagtgc c                                               21

<210> SEQ ID NO 22
<211> LENGTH: 26
<212> TYPE: DNA
<213> ORGANISM: Artificial Sequence
<220> FEATURE:
<223> OTHER INFORMATION: Oligo ID NO: 022

<400> SEQUENCE: 22
ggtggataaa ttcgcaaggg tatcat                                          26

<210> SEQ ID NO 23
<211> LENGTH: 27
<212> TYPE: DNA
<213> ORGANISM: Artificial Sequence
<220> FEATURE:
<223> OTHER INFORMATION: Oligo ID NO: 023

<400> SEQUENCE: 23
acctatcaca tcttttttcca aaactgc                                        27
```

<210> SEQ ID NO 24
<211> LENGTH: 27
<212> TYPE: DNA
<213> ORGANISM: Artificial Sequence
<220> FEATURE:
<223> OTHER INFORMATION: Oligo ID NO: 024

<400> SEQUENCE: 24
gcagttttgg aaaaagatgt gataggt          27

<210> SEQ ID NO 25
<211> LENGTH: 37
<212> TYPE: DNA
<213> ORGANISM: Artificial Sequence
<220> FEATURE:
<223> OTHER INFORMATION: Oligo ID NO: 025

<400> SEQUENCE: 25
ctgtcagacc aagtttactc atatatactt tagattg          37

<210> SEQ ID NO 26
<211> LENGTH: 16
<212> TYPE: DNA
<213> ORGANISM: Artificial Sequence
<220> FEATURE:
<223> OTHER INFORMATION: Oligo ID NO: 026

<400> SEQUENCE: 26
gccagccatc tgttgt          16

<210> SEQ ID NO 27
<211> LENGTH: 16
<212> TYPE: DNA
<213> ORGANISM: Artificial Sequence
<220> FEATURE:
<223> OTHER INFORMATION: Oligo ID NO: 027

<400> SEQUENCE: 27
ggagtggcac cttcca          16

<210> SEQ ID NO 28
<211> LENGTH: 21
<212> TYPE: DNA
<213> ORGANISM: Artificial Sequence
<220> FEATURE:
<223> OTHER INFORMATION: Oligo ID NO: 028

<400> SEQUENCE: 28
tcccccgtgc cttccttgac c          21

<210> SEQ ID NO 29
<211> LENGTH: 1866
<212> TYPE: DNA
<213> ORGANISM: Artificial Sequence
<220> FEATURE:
<223> OTHER INFORMATION: rep2 gene

<400> SEQUENCE: 29
atgccggggt tttacgagat tgtgattaag gtccccagcg accttgacga gcatctgccc          60
ggcatttctg acagctttgt gaactgggtg ccgagaaagg aatgggagtt gccgccagat          120
tctgacatgg atctgaatct gattgagcag gcacccctga ccgtggccga aagctgcag          180 cgcgactttc tgacggaatg gcgccgtgtg agtaaggccc cggaggccct tttctttgtg          240

-continued

```
caatttgaga agggagagag ctacttccac atgcacgtgc tcgtggaaac caccggggtg      300
aaatccatgg ttttgggacg tttcctgagt cagattcgcg aaaaactgat tcagagaatt      360
taccgcggga tcgagccgac tttgccaaac tggttcgcgg tcacaaagac cagaaatggc      420
gccggaggcg ggaacaaggt ggtggatgag tgctacatcc ccaattactt gctccccaaa      480
acccagcctg agctccagtg ggcgtggact aatatggaac agtatttaag cgcctgtttg      540
aatctcacgg agcgtaaacg gttggtggcc agcatctgac gcacgtgtc gcagacgcag       600 gagcagaaca aagagaatca gaatcccaat tctgatgcgc cggtgatcag atcaaaaact      660
tcagccaggt acatggagct ggtcgggtgg ctcgtggaca aggggattac ctcggagaag      720
cagtggatcc aggaggacca ggcctcatac atctccttca atgcggcctc caactcgcgg      780
tcccaaatca aggctgcctt ggacaatgcg ggaaagatta tgagcctgac taaaaccgcc      840
cccgactacc tggtgggcca gcagcccgtg gaggacattt ccagcaatcg gatttataaa      900
attttggaac taaacgggta cgatcccaa tatgcggctt ccgtctttct gggatgggcc       960
acgaaaaagt tcggcaagag gaacaccatc tggctgtttg ggcctgcaac taccgggaag     1020
accaacatcg cggaggccat agcccacact gtgcccttct acgggtgcgt aaactggacc     1080
aatgagaact ttcccttcaa cgactgtgtc gacaagatgg tgatctggtg ggaggagggg     1140
aagatgaccg ccaaggtcgt ggagtcggcc aaagccattc tcggaggaag caaggtgcgc     1200
gtggaccaga atgcaagtc ctcggcccag atagacccga ctcccgtgat cgtcacctcc      1260
aacaccaaca tgtgcgccgt gattgacggg aactcaacga ccttcgaaca ccagcagccg     1320
ttgcaagacc ggatgttcaa atttgaactc acccgccgtc tggatcatga ctttgggaag     1380
gtcaccaagc aggaagtcaa agacttttc cggtgggcaa aggatcacgt ggttgaggtg      1440
gagcatgaat tctacgtcaa aaagggtgga gccaagaaaa gacccgcccc cagtgacgca     1500
gatataagtg agcccaaacg ggtgcgcgag tcagttgcgc agccatcgac gtcagacgcg     1560
gaagcttcga tcaactacgc agacaggtac caaaacaaat gttctcgtca cgtgggcatg     1620
aatctgatgc tgtttccctg cagacaatgc gagagaatga atcagaattc aaatatctgc     1680
ttcactcacg gacagaaaga ctgtttagag tgctttcccg tgtcagaatc tcaacccgtt     1740
tctgtcgtca aaaaggcgta tcagaaactg tgctacattc atcatatcat gggaaaggtg     1800
ccagacgctt gcactgcctg cgatctggtc aatgtggatt tggatgactg catctttgaa     1860
caataa                                                                1866
```

<210> SEQ ID NO 30
<211> LENGTH: 2208
<212> TYPE: DNA
<213> ORGANISM: Artificial Sequence
<220> FEATURE:
<223> OTHER INFORMATION: cap2 gene

<400> SEQUENCE: 30

```
atggctgccg atggttatct tccagattgg ctcgaggaca ctctctctga aggaataaga       60
cagtggtgga agctcaaacc tggcccacca ccaccaaagc ccgcagagcg cataaggac       120 gacagcaggt tcttgtgct tcctgggtac aagtacctcg acccttcaa cggactcgac        180 aagggagagc cggtcaacga ggcagacgcc gcggccctcg agcacgacaa agcctacgac      240
cggcagctcg acagcggaga caacccgtac ctcaagtaca accacgccga cgcggagttt      300
caggagcgct taaagaaga tacgtctttt ggggcaacc tcggacgagc agtcttccag        360
gcgaaaaaga gggttcttga acctctgggc ctggttgagg aacctgttaa gacggctccg      420
```

```
ggaaaaaaga ggccggtaga gcactctcct gtggagccag actcctcctc gggaaccgga       480
aaggcgggcc agcagcctgc aagaaaaaga ttgaattttg gtcagactgg agacgcagac       540
tcagtacctg accccagcc tctcggacag ccaccagcag cccctctgg tctgggaact        600 aatacgatgg ctacaggcag tggcgcacca atggcagaca ataacgaggg cgccgacgga       660
gtgggtaatt cctcgggaaa ttggcattgc gattccacat ggatgggcga cagagtcatc       720
accaccagca cccgaacctg ggccctgccc acctacaaca accacctcta caaacaaatt       780
tccagccaat caggagcctc gaacgacaat cactactttg ctacagcac cccttggggg        840 tattttgact tcaacagatt ccactgccac ttttcaccac gtgactggca aagactcatc       900
aacaacaact ggggattccg acccaagaga ctcaacttca agctctttaa cattcaagtc       960
aaagaggtca cgcagaatga cggtacgacg acgattgcca ataaccttac cagcacggtt      1020
caggtgttta ctgactcgga gtaccagctc ccgtacgtcc tcggctcggc catcaagga      1080 tgcctcccgc cgttcccagc agacgtcttc atggtgccac agtatggata cctcaccctg      1140
aacaacggga gtcaggcagt aggacgctct tcatttact gcctggagta ctttccttct       1200
cagatgctgc gtaccggaaa caactttacc ttcagctaca cttttgagga cgttcctttc       1260
cacagcagct acgctcacag ccagagtctg accgtctca tgaatcctct catcgaccag        1320
tacctgtatt acttgagcag aacaaacact ccaagtggaa ccaccacgca gtcaaggctt      1380
cagttttctc aggccggagc gagtgacatt cgggaccagt ctaggaactg gcttcctgga      1440
ccctgttacc gccagcagcg agtatcaaag acatctgcgg ataacaacaa cagtgaatac      1500
tcgtggactg gagctaccaa gtaccacctc aatggcagag actctctggt gaatccgggc      1560
ccggccatgg caagccacaa ggacgatgaa gaaagtttt tcctcagag cggggttctc       1620 atctttggga agcaaggctc agagaaaaca aatgtggaca ttgaaaaggt catgattaca      1680
gacgaagagg aaatcaggac aaccaatccc gtgctacgg agcagtatgg ttctgtatct      1740
accaacctcc agagaggcaa cagacaagca gctaccgcag atgtcaacac acaaggcgtt      1800
cttccaggca tggtctggca ggacagagat gtgtaccttc agggccccat ctgggcaaag      1860
attccacaca cggacggaca ttttcacccc tctcccctca tgggtggatt cggacttaaa      1920
caccctcctc cacagattct catcaagaac accccggtac ctgcgaatcc ttcgaccacc      1980
ttcagtgcgg caaagtttgc ttccttcatc acacagtact ccacgggaca ggtcagcgtg      2040
gagatcgagt gggagctgca gaaggaaaac agcaaacgct ggaatcccga aattcagtac      2100
acttccaact acaacaagtc tgttaatgtg gactttactg tggacactaa tggcgtgtat      2160
tcagagcctc gccccattgg caccagatac ctgactcgta atctgtaa                   2208
```

<210> SEQ ID NO 31
<211> LENGTH: 2175
<212> TYPE: DNA
<213> ORGANISM: Artificial Sequence
<220> FEATURE:
<223> OTHER INFORMATION: cap5 gene

<400> SEQUENCE: 31

```
atgtcttttg ttgatcaccc tccagattgg ttggaagaag ttggtgaagg tcttcgcgag        60
tttttgggcc ttgaagcggg cccaccgaaa ccaaaaccca atcagcagca tcaagatcaa       120
gcccgtggtc ttgtgctgcc tggttataac tatctcggac ccggaaacgg tctcgatcga       180
ggagagcctg tcaacagggc agacgaggtc gcgcgagagc acgacatctc gtacaacgag      240
```

```
cagcttgagg cgggagacaa cccctacctc aagtacaacc acgcggacgc cgagtttcag    300
gagaagctcg ccgacgacac atccttcggg ggaaacctcg gaaaggcagt ctttcaggcc    360
aagaaaaggg ttctcgaacc ttttggcctg gttgaagagg gtgctaagac ggcccctacc    420
ggaaagcgga tagacgacca cttttccaaaa agaaagaagg ctcggaccga agaggactcc    480
aagccttcca cctcgtcaga cgccgaagct ggacccagcg gatcccagca gctgcaaatc    540
ccagcccaac cagcctcaag tttgggagct gatacaatgt ctgcgggagg tggcggccca    600
ttgggcgaca ataaccaagg tgccgatgga gtgggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag caccccctgg gggtactttg actttaaccg cttccacagc    840
cactggagcc cccgagactg gcaaagactc atcaacaact actggggctt cagacccgg    900 tccctcagag tcaaaatctt caacattcaa gtcaaagagg tcacggtgca ggactccacc    960
accaccatcg ccaacaacct cacctccacc gtccaagtgt ttacgacga cgactaccag    1020 ctgcccctacg tcgtcggcaa cgggaccgag ggatgcctgc cggccttccc tccgcaggtc    1080
tttacgctgc cgcagtacgg ttacgcgacg ctgaaccgcg acaacacaga aaatcccacc    1140
gagaggagca gcttcttctg cctagagtac tttcccagca agatgctgag aacgggcaac    1200
aactttgagt ttacctacaa cttttgaggag gtgcccttcc actccagctt cgctcccagt    1260
cagaacctgt tcaagctggc caacccgctg gtggaccagt acttgtaccg cttcgtgagc    1320
acaaataaca ctggcggagt ccagttcaac aagaacctgg ccgggagata cgccaacacc    1380
tacaaaaact ggttcccggg gcccatgggc cgaacccagg gctggaacct gggctccggg    1440
gtcaaccgcg ccagtgtcag cgccttcgcc acgaccaata ggatgagct cgagggcgcg    1500 agttaccagg tgccccgca gccgaacggc atgaccaaca cctccagggg cagcaacacc    1560
tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cgtacaacct ccaggaaatc gtgcccggca cgtgtggat ggagagggac    1800 gtgtacctcc aaggacccat ctgggccaag atccccagaga cggggcgca ctttcacccc    1860 tctccggcca tgggcggatt cggactcaaa cacccaccgc ccatgatgct catcaagaac    1920
acgcctgtgc ccgaaatat caccagcttc tcggacgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca acgaccccca gtttgtggac    2100
tttgccccgg acagcaccgg ggaatacaga accaccgac ctatcggaac ccgatacctt    2160
acccgacccc tttaa                                                     2175
```

<210> SEQ ID NO 32
<211> LENGTH: 2217
<212> TYPE: DNA
<213> ORGANISM: Artificial Sequence
<220> FEATURE:
<223> OTHER INFORMATION: cap8 gene

<400> SEQUENCE: 32

```
atggctgccg atggttatct tccagattgg ctcgaggaca acctctctga gggcattcgc     60
gagtggtggg cgctgaaacc tggagccccg aagcccaaag ccaaccagca aaagcaggac    120
```

```
gacggccggg gtctggtgct tcctggctac aagtacctcg gacccttcaa cggactcgac      180
aagggggagc ccgtcaacgc ggcggacgca gcggcccctcg agcacgacaa ggcctacgac     240
cagcagctgc aggcgggtga caatccgtac ctgcggtata ccacgccga cgccgagttt      300
caggagcgtc tgcaagaaga tacgtctttt gggggcaacc tcgggcgagc agtcttccag     360
gccaagaagc gggttctcga acctctcggt ctggttgagg aaggcgctaa cggctcct      420
ggaaagaaga gaccggtaga gccatcaccc cagcgttctc cagactcctc tacgggcatc    480
ggcaagaaag ccaacagcc cgccagaaaa agactcaatt ttggtcagac tggcgactca     540
gagtcagttc cagacctca acctctcgga gaacctccag cagcgccctc tggtgtggga     600
cctaatacaa tggctgcagg cggtggcgca ccaatggcag acaataacga aggcgccgac    660
ggagtgggta gttcctcggg aaattggcat tgcgattcca catggctggg cgacagagtc    720
atcaccacca gcacccgaac ctgggccctg cccacctaca caaccaccct ctacaagcaa    780
atctccaacg ggacatcggg aggagccacc aacgacaaca cctacttcgg ctacagcacc    840
cccctgggggt attttgactt taacagattc cactgccact tttcaccacg tgactggcag    900
cgactcatca caacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca caacggtag tcaggccgtg ggacgctcct ccttctactg cctggaatac   1200
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg   1380
cagactctgg gcttcagcca aggtgggcct aatacaatgg ccaatcaggc aaagaactgg   1440
ctgccaggac cctgttaccg ccaacaacgc gtctcaacga caaccgggca aacaacaat   1500
agcaactttg cctggactgc tgggaccaaa taccatctga atggaagaaa ttcattggct   1560
aatcctggca tcgctatggc aacacacaaa gacgacgagg agcgttttttt tcccagtaac   1620
gggatcctga tttttggcaa acaaaatgct gccagagaca atgcggatta cagcgatgtc   1680
atgctcacca gcgaggaaga aatcaaaacc actaaccctg tggctacaga ggaatacggt   1740
atcgtggcag ataacttgca gcagcaaaac acggctcctc aaattggaac tgtcaacagc   1800
cagggggcct acccggtat ggtctggcag aaccgggacg tgtacctgca gggtcccatc   1860
tgggccaaga ttcctcacac ggacggcaac ttccacccgt ctccgctgat gggcggcttt   1920
ggcctgaaac atcctccgcc tcagatcctg atcaagaaca cgcctgtacc tgcggatcct   1980
ccgaccacct tcaaccagtc aaagctgaac tctttcatca cgcaatacag caccggacag   2040
gtcagcgtgg aaattgaatg ggagctgcag aaggaaaaca gcaagcgctg gaaccccgag   2100
atccagtaca cctccaacta ctacaaatct acaagtgtgg actttgctgt taatacagaa   2160
ggcgtgtact ctgaaccccg ccccattggc acccgttacc tcacccgtaa tctgtaa      2217
```

<210> SEQ ID NO 33
<211> LENGTH: 2211
<212> TYPE: DNA
<213> ORGANISM: Artificial Sequence
<220> FEATURE:
<223> OTHER INFORMATION: cap9 gene

<400> SEQUENCE: 33

```
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggagc cggtcaacgc agcagacgcg gcggccctcg agcacgacaa ggcctacgac    240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag ccccctcagg tgtgggatct   600
cttacaatgg cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg tcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaaggaa gaggaccgtt tctttcctt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcagaccg gctgggttca aaaccaagga   1800
atacttccgg gtatggtttg gcaggacaga gatgtgtacc tgcaaggacc catttgggcc   1860
aaaattcctc acacgacgg caactttcac ccttctccgc tgatgggagg gtttggaatg   1920
aagcacccgc tcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a           2211
```

<210> SEQ ID NO 34
<211> LENGTH: 5340

```
<212> TYPE: DNA
<213> ORGANISM: Artificial Sequence
<220> FEATURE:
<223> OTHER INFORMATION: E2a gene

<400> SEQUENCE: 34
cgaccgcacc ctgtgacgaa agccgcccgc aagctgcgcc cctgagttag tcatctgaac    60
ttcggcctgg gcgtctctgg gaagtaccac agtggtggga gcgggacttt cctggtacac   120
cagggcagcg ggccaactac ggggattaag gttattacga ggtgtggtgg taatagccgc   180
ctgttccaag agaattcggt ttcggtgggc gcggattccg ttgacccggg atatcatgtg   240
gggtcccgcg ctcatgtagt ttattcgggt tgagtagtct tgggcagctc cagccgcaag   300
tcccatttgt ggctggtaac tccacatgta gggcgtggga atttccttgc tcataatggc   360
gctgacgaca ggtgctggcg ccgggtgtgg ccgctggaga tgacgtagtt ttcgcgctta   420
aatttgagaa agggcgcgaa actagtcctt aagagtcagc gcgcagtatt tactgaagag   480
agcctccgcg tcttccagcg tgcgccgaag ctgatcttcg cttttgtgat acaggcagct   540
gcgggtgagg gatcgcagag acctgttttt tattttcagc tcttgttctt ggccctgct    600
ctgttgaaat atagcataca gagtgggaaa atcctgtttt ctaagctcgc gggtcgatac   660
gggttcgttg gcgccagac gcagcgctcc tcctcctgct gctgccgccg ctgtggattt    720
cttgggcttt gtcagagtct tgctatccgg tcgcctttgc ttctgtgtgg ccgctgctgt   780
tgctgccgct gccgctgccg ccggtgcagt atgggctgta gagatgacgg tagtaatgca   840
ggatgttacg ggggaaggcc acgccgtgat ggtagagaag aaagcggcgg gcgaaggaga   900
tgttgccccc acagtcttgc aagcaagcaa ctatggcgtt cttgtgcccg cgccatgagc   960
ggtagccttg gcgctgttgt tgctcttggg ctaacggcgg cggctgcttg gacttaccgg  1020
ccctggttcc agtggtgtcc catctacggt tgggtcggcg aacgggcagt gccggcggcg  1080
cctgaggagc ggaggttgta gccatgctgg aacggttgc cgatttctgg ggcgccggcg   1140
aggggaatgc gaccgagggt gacggtgttt cgtctgacac ctcttcgacc tcggaagctt  1200
cctcgtctag gctctcccag tcttccatca tgtcctcctc ctcctcgtcc aaaacctcct  1260
ctgcctgact gtcccagtat tcctcctcgt ccgtgggtgg cggcggcagc tgcagcttct  1320
tttgggtgc catcctggga agcaaggggcc cgcggctgct gctgataggg ctgcggcggc  1380
gggggattg ggttgagctc ctcgccggac tgggggtcca agtaaacccc ccgtcccttt  1440
cgtagcagaa actcttggcg ggctttgttg atggcttgca attggccaag aatgtggccc  1500
tgggtaatga cgcaggcggt aagctccgca tttggcgggc gggattggtc ttcgtagaac  1560
ctaatctcgt gggcgtggta gtcctcaggt acaaatttgc gaaggtaagc cgacgtccac  1620
agccccggag tgagtttcaa ccccggagcc gcggactttt cgtcaggcga gggaccctgc  1680
agctcaaagg taccgataat ttgactttcg ttaagcagct gcgaattgca aaccagggag  1740
cggtgcgggg tgcataggtt gcagcgacag tgacactcca gtagaccgtc accgctcacg  1800
tcttccatta tgtcagagtg gtaggcaagg tagttggcta gctgcagaag gtagcagtgg  1860
ccccaaagcg gcggagggca ttcgcggtac ttaatgggca caagtcgct aggaagtgca   1920
cagcaggtgg cgggcaagat tcctgagcgc tctaggataa agttcctaaa gttctgcaac  1980
atgctttgac tggtgaagtc tggcagaccc tgttgcaggg ttttaagcag gcgttcgggg  2040
aaaatgatgt ccgccaggtg cgcggccacg gagcgctcgt tgaaggccgt ccataggtcc  2100
ttcaagtttt gctttagcag tttctgcagc tccttgaggt tgcactcctc caagcactgc  2160
```

```
tgccaaacgc ccatggccgt ctgccaggtg tagcatagaa ataagtaaac gcagtcgcgg      2220
acgtagtcgc ggcgcgcctc gcccttgagc gtggaatgaa gcacgttttg cccaaggcgg      2280
ttttcgtgca aaattccaag gtaggagacc aggttgcaga gctccacgtt ggagatcttg      2340
caggcctggc gtacgtagcc ctgtcgaaag gtgtagtgca atgtttcctc tagcttgcgc      2400
tgcatctccg ggtcagcaaa gaaccgctgc atgcactcaa gctccacggt aacgagcact      2460
gcggccatca ttagtttgcg tcgctcctcc aagtcggcag gctcgcgcgt ttgaagccag      2520
cgcgctagct gctcgtcgcc aactgcgggt aggccctcct ctgtttgttc ttgcaaattt      2580
gcatccctct ccaggggctg cgcacggcgc acgatcagct cactcatgac tgtgctcatg      2640
accttggggg gtaggttaag tgccgggtag gcaaagtggg tgacctcgat gctgcgtttt      2700
agtacggcta ggcgcgcgtt gtcaccctcg agttccacca acactccaga gtgactttca      2760
ttttcgctgt tttcctgttg cagagcgttt gccgcgcgct tctcgtcgcg tccaagaccc      2820
tcaaagattt ttggcacttc gttgagcgag gcgatatcag gtatgacagc gccctgccgc      2880
aaggccagct gcttgtccgc tcggctgcgg ttggcacggc aggatagggg tatcttgcag      2940
ttttggaaaa agatgtgata ggtggcaagc acctctggca cggcaaatac ggggtagaag      3000
ttgaggcgcg ggttgggctc gcatgtgccg ttttcttggc gtttgggggg tacgcgcggt      3060
gagaataggt ggcgttcgta ggcaaggctg acatccgcta tggcgagggg cacatcgctg      3120
cgctcttgca acgcgtcgca gataatggcg cactggcgct gcagatgctt caacagcacg      3180
tcgtctccca catctaggta gtcgccatgc cttcgtccc  ccgcccgac ttgttcctcg      3240 tttgcctctg cgttgtcctg gtcttgcttt ttatcctctg ttggtactga gcggcctcg      3300 tcgtcttcgc ttacaaaacc tgggtcctgc tcgataatca cttcctcctc ctcaagcggg      3360
ggtgcctcga cggggaaggt ggtaggcgcg ttggcggcat cggtggaggc ggtggtggcg      3420
aactcagagg gggcggttag gctgtccttc ttctcgactg actccatgat cttttttctgc     3480 ctataggaga aggaaatggc cagtcgggaa gaggagcagc gcgaaaccac ccccgagcgc      3540
ggacgcggtg cggcgcgacg tcccccaacc atggaggacg tgtcgtcccc gtcccgtcg      3600 ccgccgcctc cccgggcgcc cccaaaaaag cggatgaggc ggcgtatcga gtccgaggac      3660
gaggaagact catcacaaga cgcgctggtg ccgcgcacac ccagcccgcg gccatcgacc      3720 tcggcggcg atttggccat tgcgcccaag aagaaaaaga gcgcccttc tcccaagccc       3780 gagcgcccgc catcaccaga ggtaatcgtg gacagcgagg aagaaagaga agatgtggcg      3840
ctacaaatgg tgggtttcag caacccaccg gtgctaatca agcatggcaa aggaggtaag      3900
cgcacagtgc ggcggctgaa tgaagacgac ccagtggcgc gtggtatgcg gacgcaagag      3960
gaagaggaag agcccagcga agcggaaagt gaaattacgg tgatgaaccc gctgagtgtg      4020
ccgatcgtgt ctgcgtggga aagggcatg gaggctgcgc gcgcgctgat ggacaagtac      4080
cacgtggata acgatctaaa ggcgaacttc aaactactgc ctgaccaagt ggaagctctg      4140
gcggccgtat gcaagacctg gctgaacgag gagcaccgcg ggttgcagct gaccttcacc      4200
agcaacaaga cctttgtgac gatgatgggg cgattcctgc aggcgtacct gcagtcgttt      4260
gcagaggtga cctacaagca tcacgagccc acggctgcg cgttgtggct gcaccgctgc      4320
gctgagatcg aaggcgagct taagtgtcta cacggaagca ttatgataaa taaggagcac      4380
gtgattgaaa tggatgtgac gagcgaaaac gggcagcgcg cgctgaagga gcagtctagc      4440
aaggccaaga tcgtgaagaa ccggtggggc cgaaatgtgg tgcagatctc caacaccgac      4500
gcaaggtgct gcgtgcacga cgcggcctgt ccggccaatc agttttccgg caagtcttgc      4560
```

```
ggcatgttct tctctgaagg cgcaaaggct caggtggctt ttaagcagat caaggctttt    4620
atgcaggcgc tgtatcctaa cgcccagacc gggcacggtc acctttgat gccactacgg     4680 tgcgagtgca actcaaagcc tgggcacgcg ccctttttgg aaggcagct accaaagttg     4740 actccgttcg ccctgagcaa cgcggaggac ctggacgcgg atctgatctc cgacaagagc    4800
gtgctggcca gcgtgcacca cccggcgctg atagtgttcc agtgctgcaa ccctgtgtat    4860
cgcaactcgc gcgcgcaggg cggaggcccc aactgcgact tcaagatatc ggcgcccgac    4920
ctgctaaacg cgttggtgat ggtgcgcagc ctgtggagtg aaaacttcac cgagctgccg    4980
cggatggttg tgcctgagtt taagtggagc actaaacacc agtatcgcaa cgtgtccctg    5040
ccagtggcgc atagcgatgc gcggcagaac ccctttgatt tttaaacggc gcagacggca    5100
agggtggggg taaataatca cccgagagtg tacaaataaa agcatttgcc tttattgaaa    5160
gtgtctctag tacattattt ttacatgttt ttcaagtgac aaaaagaagt ggcgctccta    5220
atctgcgcac tgtggctgcg gaagtagggc gagtggcgct ccaggaagct gtagagctgt    5280
tcctggttgc gacgcagggt gggctgtacc tggggactgt tgagcatgga gttgggtacc    5340
```

<210> SEQ ID NO 35
<211> LENGTH: 3037
<212> TYPE: DNA
<213> ORGANISM: Artificial Sequence
<220> FEATURE:
<223> OTHER INFORMATION: E4 gene

<400> SEQUENCE: 35

```
gttttagggc ggagtaactt gtatgtgttg ggaattgtag ttttcttaaa atgggaagtt      60
acgtaacgtg ggaaaacgga agtgacgatt tgaggaagtt gtgggttttt tggctttcgt    120
ttctgggcgt aggttcgcgt gcggtttct gggtgttttt tgtggacttt aaccgttacg     180
tcatttttta gtcctatata tactcgctct gcacttggcc cttttttaca ctgtgactga    240
ttgagctggt gccgtgtcga gtggtgtttt tttaataggt tttctttttt actggtaagg    300
ctgactgtta tggctgccgc tgtggaagcg ctgtatgttg ttctggagcg ggagggtgct    360
attttgccta ggcaggaggg ttttttcaggt gtttatgtgt ttttctctcc tattaatttt    420 gttataccte ctatggggc tgtaatgttg tctctacgcc tgcgggtatg tattccccg      480 ggctatttcg gtcgcttttt agcactgacc gatgtgaatc aacctgatgt gtttaccgag    540
tcttacatta tgactccgga catgaccgag gagctgtcgg tggtgctttt taatcacggt    600
gaccagtttt tttacggtca cgccggcatg gccgtagtcc gtcttatgct tataagggtt    660 gttttttcctg ttgtaagaca ggcttctaat gtttaaatgt tttttttgtta ttttatttttg   720 tgtttatgca gaaacccgca gacatgtttg agagaaaaat ggtgtctttt tctgtggtgg    780
ttccggagct tacctgcctt tatctgcatg agcatgacta cgatgtgctt tcttttttgc    840
gcgaggcttt gcctgatttt ttgagcagca ccttgcattt tatatcgccg cccatgcaac    900
aagcttacat cggggctacg ctggttagca tagctccgag tatgcgtgtc ataatcagtg    960
tgggttcttt tgtcatggtt cctggcgggg aagtggccgc gctggtccgt gcagacctgc   1020
acgattatgt tcagctggcc ctgcgaaggg acctacggga tcgcggtatt tttgttaatg   1080
ttccgctttt gaatcttata caggtctgtg aggaacctga attttgcaa tcatgattcg    1140 ctgcttgagg ctgaaggtgg agggcgctct ggagcagatt tttacaatgg ccggacttaa    1200
tattcgggat ttgcttagag atatattgag aaggtggcga gatgagaatt attttgggcat   1260
```

```
ggttgaaggt gctggaatgt ttatagagga gattcaccct gaagggttta gcctttacgt    1320
ccacttggac gtgagggccg tttgcctttt ggaagccatt gtgcaacatc ttacaaatgc    1380
cattatctgt tctttggctg tagagtttga ccacgccacc ggaggggagc gcgttcactt    1440
aatagatctt catttgagg ttttggataa tcttttggaa taaaaaaaaa aacatggttc      1500
ttccagctct tcccgctcct cccgtgtgtg actcgcagaa cgaatgtgta ggttggctgg    1560
gtgtggctta ttctgcggtg gtggatgtta tcagggcagc ggcgcatgaa ggagtttaca    1620
tagaacccga agccaggggg cgcctggatg ctttgagaga gtggatatac tacaactact    1680
acacagagcg atctaagcgg cgagaccgga gacgcagatc tgtttgtcac gcccgcacct    1740
ggttttgctt caggaaatat gactacgtcc ggcgttccat ttggcatgac actacgacca    1800
acacgatctc ggttgtctcg gcgcactccg tacagtaggg atcgtctacc tcctttt gag    1860 acagaaaccc gcgctaccat actggaggat catccgctgc tgcccgaatg taacactttg    1920
acaatgcaca acgtgagtta cgtgcgaggt cttccctgca gtgtgggatt tacgctgatt    1980
caggaatggg ttgttccctg ggatatggtt ctaacgcggg aggagcttgt aatcctgagg    2040
aagtgtatgc acgtgtgcct gtgttgtgcc aacattgata tcatgacgag catgatgatc    2100
catggttacg agtcctgggc tctccactgt cattgttcca gtcccggttc cctgcagtgt    2160
atagccggcg ggcaggtttt ggccagctgg tttaggatgg tggtggatgg cgccatgttt    2220
aatcagaggt ttatatggta ccgggaggtg gtgaattaca acatgccaaa agaggtaatg    2280
tttatgtcca gcgtgtttat gaggggtcgc cacttaatct acctgcgctt gtggtatgat    2340
ggccacgtgg gttctgtggt ccccgccatg agctttggat acagcgcctt gcactgtggg    2400
attttgaaca atattgtggt gctgtgctgc agttactgtg ctgatttaag tgagatcagg    2460
gtgcgctgct gtgcccggag gacaaggcgc cttatgctgc gggcggtgcg aatcatcgct    2520
gaggagacca ctgccatgtt gtattcctgc aggacggagc ggcggcggca gctttatt      2580 cgcgcgctgt gcagcacca ccgccctatc ctgatgcacg attatgactc tacccccatg    2640
taggcgtgga cttctccttc gccgcccgtt aagcaaccgc aagttggaca gcagcctgtg    2700
gctcagcagc tggacagcga catgaactta agtgagctgc cggggagtt tattaatatc    2760 actgatgagc gtttggctcg acaggaaacc gtgtggaata taacacctaa gaatatgtct    2820
gttacccatg atatgatgct ttttaaggcc agccggggag aaaggactgt gtactctgtg    2880
tgttgggagg gaggtggcag gttgaatact agggttctgt gagtttgatt aaggtacggt    2940
gatctgtata agctatgtgg tggtggggct atactactga atgaaaaatg acttgaaatt    3000
ttctgcaatt gaaaaataaa cacgttgaaa cataaca                             3037
```

```
<210> SEQ ID NO 36
<211> LENGTH: 731
<212> TYPE: DNA
<213> ORGANISM: Artificial Sequence
<220> FEATURE:
<223> OTHER INFORMATION: VA RNAs gene

<400> SEQUENCE: 36
atccgtagat gtacctggac atccaggtga tgccggcggc ggtggtggag gcgcgcggaa     60
agtcgcggac gcggttccag atgttgcgca gcggcaaaaa gtgctccatg gtcgggacgc    120
tctggccggt caggcgcgcg caatcgttga cgctctagac cgtgcaaaag gagagcctgt    180
aagcaagcac tcttccgtgg tctggtggat aaattcgcaa gggtatcatg gcggacgacc    240
ggggttcgag ccccgtatcc ggccgtccgc cgtgatccat gcggttaccg cccgcgtgtc    300
```

```
gaacccaggt gtgcgacgtc agacaacggg ggagtgctcc ttttggcttc cttccaggcg    360
cggcggctgc tgcgctagct ttttggcca ctggccgcgc gcagcgtaag cggttaggct     420
ggaaagcgaa agcattaagt ggctcgctcc ctgtagccgg agggttattt tccaagggtt    480
gagtcgcggg accccggtt cgagtctcgg accggccgga ctgcggcgaa cgggggtttg     540
cctccccgtc atgcaagacc ccgcttgcaa attcctccgg aaacagggac gagccccttt    600
tttgcttttc ccagatgcat ccggtgctgc ggcagatgcg ccccccctcct cagcagcggc   660 aagagcaaga gcagcggcag acatgcaggg caccctcccc tcctcctacc gcgtcaggag    720
gggcgacatc c                                                        731

<210> SEQ ID NO 37
<211> LENGTH: 861
<212> TYPE: DNA
<213> ORGANISM: Artificial Sequence
<220> FEATURE:
<223> OTHER INFORMATION: Ampicillin Resistance Gene

<400> SEQUENCE: 37
atgagtattc aacatttccg tgtcgccctt attccctttt tgcggcatt ttgccttcct      60 gttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg ggatcatgt aactcgcctt     480 gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga ataggtgcc     840 tcactgatta agcattggta a                                             861

<210> SEQ ID NO 38
<211> LENGTH: 798
<212> TYPE: DNA
<213> ORGANISM: Artificial Sequence
<220> FEATURE:
<223> OTHER INFORMATION: Kanamycin Resistance Gene

<400> SEQUENCE: 38
atgattgaac aggatggcct gcatgcgggt agcccggcag cgtgggtgga acgtctgttt      60
ggctatgatt gggcgcagca gaccattggc tgctctgatg cggcggtgtt tcgtctgagc    120
gcgcagggtc gtccggtgct gtttgtgaaa accgatctga gcggtgcgct gaacgagctg    180
caggatgaag cggcgcgtct gagctggctg gccaccaccg tgttccgtg tgcggcggtg     240 ctggatgtgg tgaccgaagc gggccgtgat tggctgctgc tgggcgaagt gccgggtcag    300
gatctgctgt ctagccatct ggcgccggca gaaaaagtga gcattatggc ggatgccatg    360
```

```
cgtcgtctgc ataccctgga cccggcgacc tgtccgtttg atcatcaggc gaaacatcgt        420
attgaacgtg cgcgtacccg tatggaagcg ggcctggtgg atcaggatga tctggatgaa        480
gaacatcagg gcctggcacc ggcagagctg tttgcgcgtc tgaaagcgag catgccggat        540
ggcgaagatc tggtggtgac ccatggtgat gcgtgcctgc cgaacattat ggtggaaaat        600
ggccgtttta gcggctttat tgattgcggc cgtctgggcg tggcggatcg ttatcaggat        660
attgcgctgg ccaccgtga tattgcggaa gaactgggcg gcgaatgggc ggatcgtttt        720
ctggtgctgt atggcattgc ggcaccggat agccagcgta ttgcgttta tcgtctgctg        780 gatgaattt tctaataa                                                      798
```